United States Patent
Lee et al.

(10) Patent No.: US 8,251,061 B2
(45) Date of Patent: Aug. 28, 2012

(54) METHODS AND SYSTEMS FOR CONTROL OF GAS THERAPY

(75) Inventors: Kent Lee, Fridley, MN (US); Jesse W. Hartley, Lino Lakes, MN (US); Jeffrey E. Stahmann, Ramsey, MN (US); Quan Ni, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1215 days.

(21) Appl. No.: 10/929,306

(22) Filed: Aug. 30, 2004

(65) Prior Publication Data
US 2005/0061323 A1 Mar. 24, 2005

Related U.S. Application Data

(60) Provisional application No. 60/504,750, filed on Sep. 18, 2003.

(51) Int. Cl.
*A61M 15/00* (2006.01)
*A61M 16/00* (2006.01)
*A61M 15/08* (2006.01)
*A62B 7/00* (2006.01)
*A62B 9/02* (2006.01)

(52) U.S. Cl. ......... 128/204.23; 128/204.18; 128/204.26; 128/205.11; 128/205.23; 128/205.24; 128/203.12; 128/203.22; 128/200.24

(58) Field of Classification Search .......... 128/204.18–204.23, 204.26, 205.11, 128/205.23, 205.24, 203.12, 203.22, 200.24
See application file for complete search history.

(56) References Cited

U.S. PATENT DOCUMENTS

| | | | |
|---|---|---|---|
| 4,312,734 A | 1/1982 | Nichols |
| 4,365,636 A | 12/1982 | Barker |
| 4,390,405 A | 6/1983 | Hahn et al. |
| 4,562,841 A | 1/1986 | Brockway et al. |
| 4,721,110 A | 1/1988 | Lampadius |
| 4,777,962 A | 10/1988 | Watson et al. |
| 4,802,485 A | 2/1989 | Bowers et al. |
| 4,807,629 A | 2/1989 | Baudino et al. |
| 4,813,427 A | 3/1989 | Schlaefke et al. |
| 4,827,935 A | 5/1989 | Geddes et al. |
| 4,830,008 A | 5/1989 | Meer |

(Continued)

FOREIGN PATENT DOCUMENTS
EP 0940155 9/1999
(Continued)

OTHER PUBLICATIONS

Reddel et al., *Analysis of Adherence to Peak Flow Monitoring When Recording of Data is Electronic*, BMJ 146-147 (2002).

(Continued)

*Primary Examiner* — Patricia Bianco
*Assistant Examiner* — Nihir Patel
(74) *Attorney, Agent, or Firm* — Hollingsworth Davis, LLC

(57) ABSTRACT

A gas therapy system involves sensing the blood gas concentration of the patient and adapting a gas therapy based on the sensed gas concentration. Disordered breathing may be detected bases on blood gas concentration, and gas or cardiac electrical therapy may be adapted to treat the detected disordered breathing. One or more of sensing the blood gas concentration, detecting disordered breathing, or adapting the therapy may be performed at least in part implantably. The gas therapy is delivered to the patient through an external respiratory device, such as a positive airway pressure device.

27 Claims, 12 Drawing Sheets

U.S. PATENT DOCUMENTS

| | | |
|---|---|---|
| 4,875,477 A | 10/1989 | Waschke et al. |
| 4,886,064 A | 12/1989 | Strandberg |
| 4,928,688 A | 5/1990 | Mower |
| 4,961,423 A | 10/1990 | Canducci |
| 4,982,738 A | 1/1991 | Griebel |
| 5,036,849 A | 8/1991 | Hauck et al. |
| 5,105,354 A | 4/1992 | Nishimura |
| 5,123,425 A | 6/1992 | Shannon, Jr. et al. |
| 5,146,918 A | 9/1992 | Kallok et al. |
| 5,174,287 A | 12/1992 | Kallok et al. |
| 5,178,156 A | 1/1993 | Takishima et al. |
| 5,183,038 A | 2/1993 | Hoffman et al. |
| 5,187,657 A | 2/1993 | Forbes |
| 5,199,424 A | 4/1993 | Sullivan et al. |
| 5,203,348 A | 4/1993 | Dahl et al. |
| 5,211,173 A | 5/1993 | Kallok et al. |
| 5,215,082 A | 6/1993 | Kallok et al. |
| 5,230,337 A | 7/1993 | Dahl et al. |
| 5,233,983 A | 8/1993 | Markowitz |
| 5,243,979 A | 9/1993 | Stein et al. |
| 5,245,995 A | 9/1993 | Sullivan et al. |
| 5,259,373 A | 11/1993 | Gruenke et al. |
| 5,284,136 A | 2/1994 | Hauck et al. |
| 5,301,677 A | 4/1994 | Hsung |
| 5,313,953 A | 5/1994 | Yomtov et al. |
| 5,334,222 A | 8/1994 | Salo et al. |
| 5,335,657 A | 8/1994 | Terry, Jr. et al. |
| 5,353,788 A | 10/1994 | Miles |
| 5,360,442 A | 11/1994 | Dahl et al. |
| 5,366,496 A | 11/1994 | Dahl et al. |
| 5,376,476 A | 12/1994 | Eylon |
| 5,388,578 A | 2/1995 | Yomtov et al. |
| 5,391,200 A | 2/1995 | KenKnight et al. |
| 5,397,342 A | 3/1995 | Heil, Jr. et al. |
| 5,398,682 A | 3/1995 | Lynn |
| 5,404,877 A | 4/1995 | Nolan et al. |
| 5,411,031 A | 5/1995 | Yomtov |
| 5,466,245 A | 11/1995 | Heemels et al. |
| 5,483,969 A | 1/1996 | Testerman et al. |
| 5,485,851 A | 1/1996 | Erickson |
| 5,517,983 A | 5/1996 | Deighan et al. |
| 5,522,382 A | 6/1996 | Sullivan et al. |
| 5,522,862 A | 6/1996 | Testerman et al. |
| 5,540,727 A | 7/1996 | Tockman et al. |
| 5,545,186 A | 8/1996 | Olson et al. |
| 5,545,202 A | 8/1996 | Dahl et al. |
| 5,549,655 A | 8/1996 | Erickson |
| 5,590,648 A | 1/1997 | Mitchell et al. |
| 5,593,431 A | 1/1997 | Sheldon |
| 5,603,732 A | 2/1997 | Dahl et al. |
| 5,605,151 A | 2/1997 | Lynn |
| 5,632,281 A | 5/1997 | Rayburn |
| 5,645,570 A | 7/1997 | Corbucci |
| 5,682,877 A * | 11/1997 | Mondry .................. 128/204.23 |
| 5,693,000 A | 12/1997 | Crosby et al. |
| 5,701,894 A | 12/1997 | Cherry et al. |
| 5,704,345 A | 1/1998 | Berthon-Jones |
| 5,715,812 A | 2/1998 | Deighan et al. |
| 5,738,102 A | 4/1998 | Lemelson |
| 5,794,615 A | 8/1998 | Estes |
| 5,800,470 A | 9/1998 | Stein et al. |
| 5,814,087 A | 9/1998 | Renirie |
| 5,826,579 A | 10/1998 | Remmers et al. |
| 5,836,987 A | 11/1998 | Baumann et al. |
| 5,844,680 A | 12/1998 | Sperling |
| 5,855,593 A | 1/1999 | Olson et al. |
| 5,861,011 A | 1/1999 | Stoop |
| 5,891,023 A | 4/1999 | Lynn |
| 5,911,218 A | 6/1999 | DiMarco |
| 5,916,243 A | 6/1999 | KenKnight et al. |
| 5,944,680 A | 8/1999 | Christopherson et al. |
| 5,964,778 A | 10/1999 | Fugoso et al. |
| 5,974,340 A | 10/1999 | Kadhiresan |
| 5,974,349 A | 10/1999 | Levine |
| 6,015,388 A | 1/2000 | Sackner et al. |
| 6,026,320 A | 2/2000 | Carlson et al. |
| 6,044,297 A | 3/2000 | Sheldon et al. |
| 6,044,298 A | 3/2000 | Salo et al. |
| 6,045,513 A | 4/2000 | Stone et al. |
| 6,047,203 A | 4/2000 | Sackner et al. |
| 6,055,454 A | 4/2000 | Heemels |
| 6,064,910 A | 5/2000 | Andersson et al. |
| 6,076,015 A | 6/2000 | Hartley et al. |
| 6,091,973 A | 7/2000 | Colla et al. |
| 6,099,479 A | 8/2000 | Christopherson et al. |
| 6,105,575 A | 8/2000 | Estes et al. |
| 6,120,441 A | 9/2000 | Griebel |
| 6,126,611 A | 10/2000 | Bourgeois et al. |
| 6,128,534 A | 10/2000 | Park et al. |
| 6,132,384 A | 10/2000 | Christopherson et al. |
| 6,141,581 A | 10/2000 | Olson et al. |
| 6,141,590 A | 10/2000 | Renirie et al. |
| 6,144,866 A | 11/2000 | Miesel et al. |
| 6,148,814 A | 11/2000 | Clemmer et al. |
| 6,155,976 A | 12/2000 | Sackner et al. |
| 6,161,042 A | 12/2000 | Hartley et al. |
| 6,165,155 A | 12/2000 | Jacobsen et al. |
| 6,168,568 B1 | 1/2001 | Gavriely |
| 6,186,142 B1 * | 2/2001 | Schmidt et al. .......... 128/204.23 |
| 6,190,326 B1 | 2/2001 | McKinnon et al. |
| 6,221,011 B1 | 4/2001 | Bardy |
| 6,236,873 B1 | 5/2001 | Holmstrom |
| 6,240,316 B1 | 5/2001 | Richmond et al. |
| 6,251,126 B1 | 6/2001 | Ottenhoff et al. |
| 6,258,039 B1 | 7/2001 | Okamoto et al. |
| 6,259,947 B1 | 7/2001 | Olson et al. |
| 6,261,238 B1 | 7/2001 | Gavriely |
| 6,264,606 B1 | 7/2001 | Ekwall et al. |
| 6,269,269 B1 | 7/2001 | Ottenhoff et al. |
| 6,270,457 B1 | 8/2001 | Bardy |
| 6,272,377 B1 | 8/2001 | Sweeney et al. |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,287,264 B1 | 9/2001 | Hoffman |
| 6,312,378 B1 | 11/2001 | Bardy |
| 6,331,536 B1 | 12/2001 | Radulovacki et al. |
| 6,336,903 B1 | 1/2002 | Bardy |
| 6,351,669 B1 | 2/2002 | Hartley et al. |
| 6,351,670 B1 | 2/2002 | Kroll |
| 6,353,759 B1 | 3/2002 | Hartley et al. |
| 6,357,444 B1 | 3/2002 | Parker |
| 6,358,203 B2 | 3/2002 | Bardy |
| 6,361,522 B1 | 3/2002 | Schneier et al. |
| 6,363,270 B1 | 3/2002 | Colla et al. |
| 6,368,284 B1 | 4/2002 | Bardy |
| 6,368,287 B1 | 4/2002 | Hadas |
| 6,371,922 B1 | 4/2002 | Baumann et al. |
| 6,375,621 B1 | 4/2002 | Sullivan |
| 6,375,623 B1 | 4/2002 | Gavriely |
| 6,397,845 B1 | 6/2002 | Burton |
| 6,398,728 B1 | 6/2002 | Bardy |
| 6,398,739 B1 | 6/2002 | Sullivan et al. |
| 6,409,675 B1 | 6/2002 | Turcott |
| 6,411,848 B2 | 6/2002 | Kramer et al. |
| 6,411,850 B1 | 6/2002 | Kay et al. |
| 6,415,183 B1 | 7/2002 | Scheiner et al. |
| 6,424,865 B1 | 7/2002 | Ding |
| 6,431,171 B1 | 8/2002 | Burton |
| 6,438,407 B1 | 8/2002 | Ousdigian et al. |
| 6,438,410 B2 | 8/2002 | Hsu et al. |
| 6,440,066 B1 | 8/2002 | Bardy |
| 6,442,413 B1 | 8/2002 | Silver |
| 6,449,503 B1 | 9/2002 | Hsu |
| 6,459,929 B1 | 10/2002 | Hopper et al. |
| 6,463,326 B1 | 10/2002 | Hartley et al. |
| 6,467,333 B2 | 10/2002 | Lewis et al. |
| 6,468,219 B1 | 10/2002 | Njemanze |
| 6,480,733 B1 | 11/2002 | Turcott |
| 6,487,443 B2 | 11/2002 | Olson et al. |
| 6,527,729 B1 | 3/2003 | Turcott |
| 6,542,775 B2 | 4/2003 | Ding et al. |
| 6,572,543 B1 | 6/2003 | Christopherson et al. |
| 6,574,507 B1 | 6/2003 | Bonnet |
| 6,589,188 B1 | 7/2003 | Street et al. |
| 6,595,928 B2 | 7/2003 | Mansy et al. |

| | | |
|---|---|---|
| 6,597,951 B2 | 7/2003 | Kramer et al. |
| 6,600,949 B1 | 7/2003 | Turcott |
| 6,606,993 B1 | 8/2003 | Wiesmann et al. |
| 6,641,542 B2 | 11/2003 | Cho et al. |
| 6,658,292 B2 | 12/2003 | Kroll et al. |
| 6,662,032 B1 | 12/2003 | Gavish et al. |
| 6,723,055 B2 | 4/2004 | Hoffman |
| 6,731,984 B2 | 5/2004 | Cho et al. |
| 6,741,885 B1 | 5/2004 | Park et al. |
| 6,748,252 B2 | 6/2004 | Lynn et al. |
| 6,752,765 B1 | 6/2004 | Jensen et al. |
| 6,773,404 B2 | 8/2004 | Poezevera et al. |
| 6,810,287 B2 | 10/2004 | Zhu et al. |
| 6,830,548 B2 | 12/2004 | Bonnet et al. |
| 6,881,192 B1 | 4/2005 | Park |
| 6,910,481 B2 | 6/2005 | Kimmel et al. |
| 6,928,324 B2 | 8/2005 | Park et al. |
| 7,025,730 B2* | 4/2006 | Cho et al. ............... 600/529 |
| 7,027,871 B2 | 4/2006 | Burnes et al. |
| 7,092,755 B2* | 8/2006 | Florio ............... 607/9 |
| 7,130,687 B2 | 10/2006 | Cho et al. |
| 7,136,704 B2 | 11/2006 | Schulman |
| 7,184,817 B2 | 2/2007 | Zhu et al. |
| 7,207,945 B2 | 4/2007 | Bardy |
| 7,225,013 B2 | 5/2007 | Geva et al. |
| 7,225,021 B1 | 5/2007 | Park et al. |
| 7,231,250 B2 | 6/2007 | Band et al. |
| 7,252,640 B2 | 8/2007 | Ni et al. |
| 7,258,670 B2 | 8/2007 | Bardy |
| 7,269,459 B1 | 9/2007 | Koh |
| 7,277,757 B2 | 10/2007 | Casavant et al. |
| 7,302,295 B2 | 11/2007 | Stahmann et al. |
| 7,575,553 B2 | 8/2009 | Stahmann et al. |
| 7,610,094 B2 | 10/2009 | Stahmann et al. |
| 2002/0147476 A1 | 10/2002 | Daum |
| 2002/0193697 A1* | 12/2002 | Cho et al. ............... 600/529 |
| 2002/0193839 A1 | 12/2002 | Cho et al. |
| 2003/0023184 A1 | 1/2003 | Pitts-Crick et al. |
| 2003/0055461 A1 | 3/2003 | Girouard et al. |
| 2003/0073919 A1 | 4/2003 | Hampton et al. |
| 2003/0083241 A1 | 5/2003 | Young et al. |
| 2003/0100925 A1 | 5/2003 | Pape et al. |
| 2003/0121519 A1 | 7/2003 | Estes et al. |
| 2003/0139780 A1 | 7/2003 | Markowitz et al. |
| 2003/0153953 A1 | 8/2003 | Park et al. |
| 2003/0153954 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171687 A1 | 9/2003 | Irie et al. |
| 2003/0195571 A1 | 10/2003 | Burnes et al. |
| 2003/0199945 A1 | 10/2003 | Ciulla |
| 2003/0204213 A1 | 10/2003 | Jensen et al. |
| 2003/0209246 A1 | 11/2003 | Schroeder et al. |
| 2004/0002742 A1 | 1/2004 | Florio |
| 2004/0030362 A1 | 2/2004 | Hill et al. |
| 2004/0039605 A1 | 2/2004 | Bardy |
| 2004/0059240 A1 | 3/2004 | Cho et al. |
| 2004/0088027 A1 | 5/2004 | Burnes et al. |
| 2004/0111040 A1 | 6/2004 | Ni et al. |
| 2004/0133079 A1 | 7/2004 | Mazar et al. |
| 2004/0138719 A1 | 7/2004 | Cho et al. |
| 2004/0163648 A1 | 8/2004 | Burton |
| 2004/0186523 A1 | 9/2004 | Florio |
| 2004/0210154 A1 | 10/2004 | Kline |
| 2005/0039745 A1 | 2/2005 | Stahmann et al. |
| 2005/0042589 A1 | 2/2005 | Hatlestad et al. |
| 2005/0043644 A1 | 2/2005 | Stahmann et al. |
| 2005/0065572 A1 | 3/2005 | Hartley et al. |
| 2005/0096707 A1* | 5/2005 | Hill et al. ............... 607/17 |
| 2005/0101841 A9 | 5/2005 | Kaylor et al. |
| 2005/0142070 A1 | 6/2005 | Hartley et al. |
| 2005/0159784 A1 | 7/2005 | Arceta |
| 2005/0240240 A1 | 10/2005 | Park et al. |
| 2006/0293714 A1 | 12/2006 | Salo et al. |
| 2007/0005114 A1 | 1/2007 | Salo et al. |
| 2007/0112388 A1 | 5/2007 | Salo |
| 2007/0150014 A1 | 6/2007 | Kramer et al. |

FOREIGN PATENT DOCUMENTS

| | | |
|---|---|---|
| EP | 1151718 | 11/2001 |
| EP | 1172125 | 1/2002 |
| WO | 99/04841 | 2/1999 |
| WO | WO 99/04841 * | 2/1999 |
| WO | WO 0001438 | 1/2000 |
| WO | WO 0017615 | 3/2000 |
| WO | WO0240096 | 5/2002 |
| WO | 02/087696 | 7/2002 |
| WO | WO 03075744 | 9/2003 |
| WO | WO 2004062485 | 7/2004 |
| WO | WO 2005028029 | 3/2005 |
| WO | WO2005053788 | 6/2005 |

OTHER PUBLICATIONS

Ajilore et al., *Nightcap: Laboratory and home-based evaluation of a portable sleep monitor*, 32 Psychophysiology, 32-98 (1995) (Abstract only).

Altshule et al., *The Effect of Position on Periodic Breathing in Chronic Cardiac Decomposition*, New Eng. Journal of Med., vol. 259, No. 22, pp. 1064-1066 (Nov. 27, 1958).

Balaban et al., *Feasibility of Screening for Sleep Apnea Using Pacemaker Impedance Sensor*, NASPE (2001).

Bradley et al, *Cardiac Output Response to Continuous Positive Airway Pressure in Congestive Heart Failure*, 145 Am. Rev. Respir. Dis. 377-382 (1992). (Abstract only).

Bradley et al., *Pathophysiologic and Therapeutic Implications of Sleep Apnea in Congestive Heart Failure*, 3 J. Cardiac Failure 223-240 (1996).

Bradley et al., *Sleep Apnea and Heart Failure, Park I: Obstructive Sleep Apnea*, 107 Circulation 1671-1678 (2003).

Buda et al., *Effect of Intrathoracic Pressure on Left Ventricular Performance*, 301 Engl. J. Med. 453-459 (1979). (Abstract only).

Calvin et al., *Positive End-Expiratory Pressure (PEEP) Does Not Depress Left Ventricular Function in Patients With Pulmonary Edema*, 124 Am. Rev. Respir. Dis. 121-128 (1981). (Abstract only).

Dark et al., *Breathing Pattern Abnormalities and Arterial Oxygen Desaturation During Sleep in the Congestive Heart Failure Syndrome*, Chest, 6:833-6 (Jun. 1987).

De Hoyos et al., *Haemodynamic Effects of Continuous Positive Airway Pressure in Humans With Normal and Impaired Left Ventricular Function*, 88 Clin. Sci. (Lond). 173-8 (1995). (Abstract only).

Garrigue et al., *Night Atrial Overdrive with DDD Pacing Results in a Significant Reduction of Sleep Apnea Episodes and QOL Improvement in Heart Failure Patients*, NASPE (2001).

Garrigue et al., *Benefit of Atrial Pacing in Sleep Apnea Syndrome*, 346 N. Engl. J. Med. 404-412 (2002).

Giardino et al., *Respiratory Sinus Arrhythmia is Associated with the Efficiency of Pulmonary Gas Exchange in Healthy Humans*, 284 Am. J. Physiol. H1585-1591 (2003).

Hanson et al., *Cardiac Gated Ventilation*, 2433 SPIE 303-308 (1995).

Hilton et al., *Evaluation of Frequency and Time-frequency Spectral Analysis of Heart Rate Variability as a Diagnostic Marker of the Sleep Apnoea Syndrome*, 37 Med. Biol. Eng. Comput. 760-769 (1999). (Abstract only).

Hoffman et al., Cheyne-Stokes Respiration in Patients Recovering from Acute Cardiogenic Pulmonary Edema, Chest, 97:410-12 (1990).

Javaheri et al., *Sleep Apnea in 81 Ambulatory Male Patients with Stable Heart Failure: Types and Their Prevalences, Consequences, and Presentations*, 97 Circulation 2154-2159 (1998).

Javaheri, "*A Mechanism of Central Sleep Apnea in Patients With Heart Failure.*" New England Journal of Medicine, Sep.; 341(13):949-54 (1999).

Junyu et al., *Posture Detection Algorithm Using Multi Axis DC-Accelerometer*, Pace vol. 22 (Apr. 1999).

Kaye et al., *Acute Effects of Continuous Positive Airway Pressure on Cardiac Sympathetic Tone in Congestive Heart Failure*, 103 Circulation 2336-2338 (2001).

Laude et al., *Effects of Breathing Pattern on Blood Pressure and Heart Rate Oscillations in Humans*, 20 Clin. Exp. Pharmol. Phisiol 619, 625 (1993). Abstract only.

Lenique et al., *Ventilatory and Hemodynamic Effects of Continuous*

Positive Airway Pressure in Left Heart Failure, 155 Am. J. Respir. Crit. Care Med. 500-505 (1997). (Abstract only).

Lugaresi et al., *Snoring*, 39 Electroencephalogr. Clin. Neurophysiol. 59-64 (1975).

Mansfield, D. et al., *Effects of Continuous Positive Airway Pressure on Lung Function in Patients with Chronic Obstructive Pulmonary Disease and Sleep Disordered Breathing*, Respirology 365-70 (1999). Abstract only.

Mehta et al., *Effects of Continuous Positive Airway Pressure on Cardiac Volumes In Patients With Ischemic and Dilated Cardiomyopathy*, 161 Am. J. Respir. Crit. Care Med. 128-134 (2000).

Naughton et al., *Effects of Continuous Positive Airway Pressure on Intrathoracic and Left Ventricular Transmural Pressure in Congestive Heart Failure*, 91 Circulation 1725-1731 (1995).

Pinsky et al., *Hemodynamic Effect of Cardiac Cycle-Specific Increases in Intrathoracic Pressure*, 6 J. Appl. Physiol. 604-612 (1986).

Potkin et al., *Effect of positive end-expiratory pressure on right and left ventricular function in patients with the adult respiratory distress syndrome*, 135 Am. Rev. Respir. Dis. 307-311 (1987). (Abstract only).

Rees et al., *Paroxysmal Nocturnal Dyspnoea and Periodic Respiration*, The Lancet, Dec. 22-29, pp. 1315-1317 (1979). (Abstract only).

Roche et al., *Screening of Obstructive Sleep Apnea Syndrome by Heart Rate Variability Analysis*, 100 Circulation 1411-1455 (1999).

Scharf, *Effects of Continuous Positive Airway Pressure on Cardiac Output in Experimental Heart Failure*, 19 Sleep S240-2 (1996). (Abstract only).

Steltner et al., *Diagnosis of Sleep Apnea by Automatic Analysis of Nasal Pressure and Forced Oscillation Impedance*. Am. Journal Respiratory Critical Care Medicine, vol. 165, pp. 940-944 (2002).

Tkacova et al., *Left Ventricular Volume In Patients with Heart Failure and Cheyne-Strokes Respiration during Sleep*, Am. Journal, Respir. Crit. Care Med., vol. 156, pp. 1549-1555 (1997).

Vanninen et al., *Cardiac Sympathovagal Balance During Sleep Apnea Episodes*, 16 Clin. Physiol. 209-216 (1996).

Verrier et al., *Sleep, dreams, and sudden death: the case for sleep as an autonomic stress test for the heart*, 31 Cardiovascular Research 181-211 (1996).

Verrier et al., *Sleep Related Cardiovascular Risk: New Home-Based Monitoring Technology for Improved Diagnosis and Therapy*, 2 A.N.E. 158-175 (1997).

Waldemark et al., *Detection of Apnea using Short Window FFT Technique and Artificial Neural Network*, 3390 SPIE International Society for Optical Engineering 122-133 (1998).

Weber et al. *Effect of CPAP and BIPAP on stroke volume in patients with obstructive sleep apnea syndrome.* Pneumolgie; 49(3):233-5. (1995) (Abstract only).

Young et al., *The Occurrence of Sleep-Disordered Breathing Among Middle Aged Adults*, N. Engl. J. Med. 1230-1235 (1993).

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769, 1999.

International Search Report dated Dec. 22, 2004 from PCT Application No. PCT/US2004/030787, 8 pages.

Office Action dated May 9, 2007 from European Application No. 04784602.7, 3 pages.

Office Action dated Jan. 10, 2008 from European Application No. 04784602.7, 3 pages.

Office Action Response dated Apr. 17, 2008 from European Application No. 04784602.7, 10 pages.

Office Action dated Dec. 21, 2008 from European Application No. 04784602.7, 6 pages.

Notice of Allowance dated Jun. 18, 2009 from U.S. Appl. No. 10/939,586, 8 pages.

Office Action Response dated Apr. 14, 2009 from U.S. Appl. No. 10/939,586, 12 pages.

Office Action dated Mar. 10, 2009 from U.S. Appl. No. 10/939,586, 3 pages.

Office Action Response dated Feb. 16, 2009 from U.S. Appl. No. 10/939,586, 12 pages.

Office Action dated Jan. 27, 2009 from U.S. Appl. No. 10/939,586, 5 pages.

Office Action dated Nov. 17, 2008 from U.S. Appl. No. 10/939,586, 12 pages.

Office Action Response dated Jul. 18, 2008 from U.S. Appl. No. 10/939,586, 10 pages.

Office Action dated Mar. 14, 2008 from U.S. Appl. No. 10/939,586, 8 pages.

Office Action dated Apr. 1, 2010 from U.S. Appl. No. 10/943,077, 3 pages.

Office Action Response dated Mar. 11, 2010 from U.S. Appl. No. 10/943,077, 12 pages.

Office Action dated Jan. 21, 2010 from U.S. Appl. No. 10/943,077, 13 pages.

Office Action Response dated Oct. 7, 2009 from U.S. Appl. No. 10/943,077, 11 pages.

Office Action dated Jul. 7, 2009 from U.S. Appl. No. 10/943,077, 13 pages.

Office Action Response dated Mar. 19, 2009 from U.S. Appl. No. 10/943,077, 11 pages.

Office Action dated Mar. 3, 2009 from U.S. Appl. No. 10/943,077, 2 pages.

Office Action dated Nov. 26, 2008 from U.S. Appl. No. 10/943,077, 12 pages.

Notice of Allowance dated Feb. 24, 2009 from U.S. Appl. No. 10/930,508, 8 pages.

Office Action Response dated Nov. 6, 2008 from U.S. Appl. No. 10/930,508, 9 pages.

Office Action dated Oct. 14, 2008 from U.S. Appl. No. 10/930,508, 4 pages.

Office Action dated Jul. 9, 2008 from U.S. Appl. No. 10/930,508, 13 pages.

Office Action Response dated Apr. 17, 2008 from U.S. Appl. No. 10/930,508, 12 pages.

Office Action dated Feb. 14, 2008 from U.S. Appl. No. 10/930,508, 12 pages.

Office Action Response dated Nov. 26, 2007 from U.S. Appl. No. 10/930,508, 12 pages.

Office Action dated Jun. 25, 2007 from U.S. Appl. No. 10/930,508, 10 pages.

File History for EP Application No. 08075738.8 as retrieved from European Patent Office Electronic File System on Jan. 21, 2011, 28 pages.

\* cited by examiner

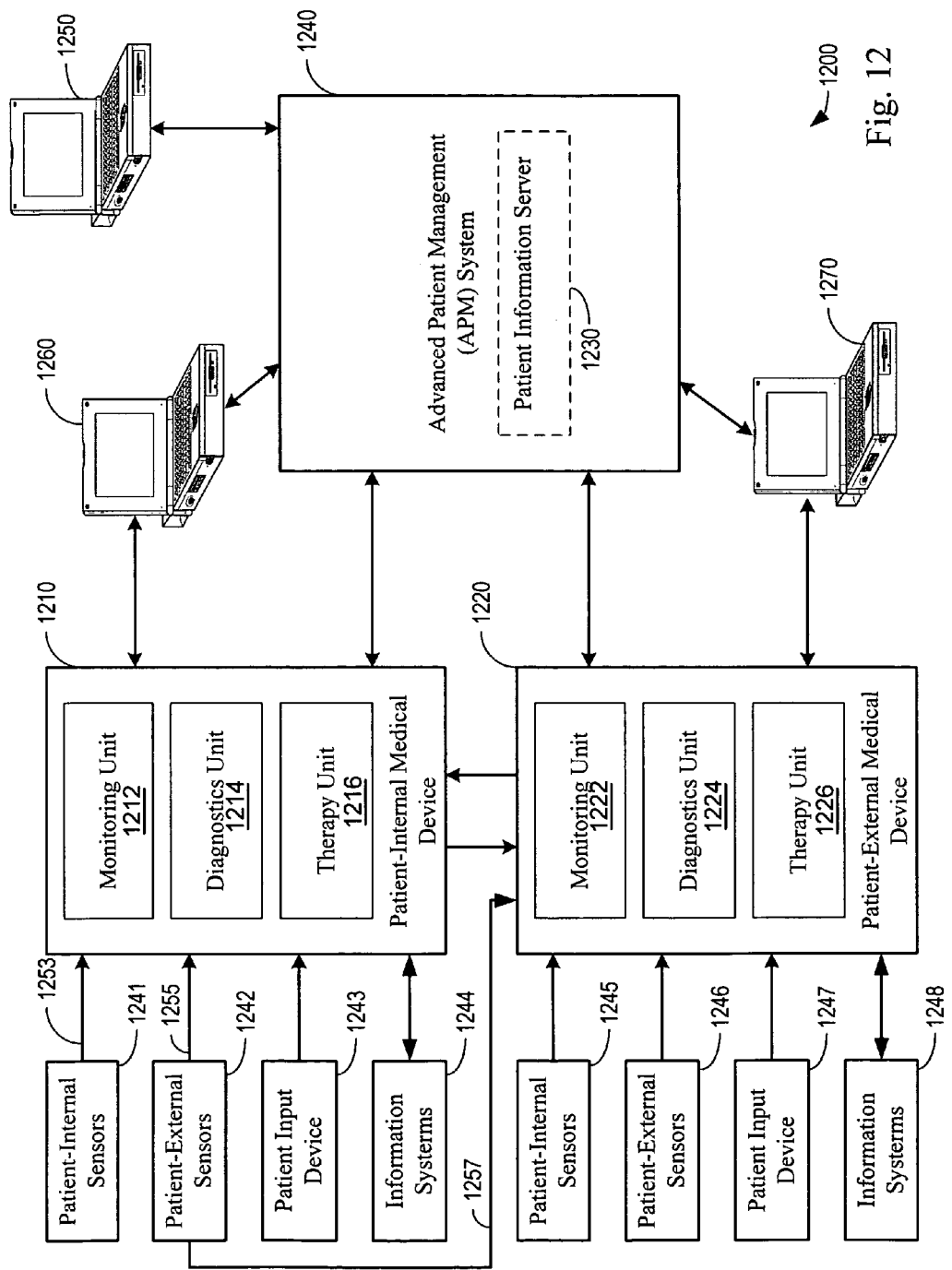

METHODS AND SYSTEMS FOR CONTROL OF GAS THERAPY

RELATED PATENT DOCUMENTS

This application claims the benefit of Provisional Patent Application Ser. No. 60/504,750 filed on Sep. 18, 2003, entitled "Methods And Systems For Control Of Gas Therapy," to which priority is claimed pursuant to 35 U.S.C. §119(e) and which is hereby incorporated herein by reference.

FIELD OF THE INVENTION

The present invention relates generally to medical gas therapy systems and methods, and more particularly to gas therapy systems incorporating an implantable component.

BACKGROUND OF THE INVENTION

The human body functions through a number of interdependent physiological systems controlled through various mechanical, electrical, and chemical processes. The metabolic state of the body is constantly changing. For example, as exercise level increases, the body consumes more oxygen and gives off more carbon dioxide. The cardiac and pulmonary systems maintain appropriate blood gas levels by making adjustments that bring more oxygen into the system and dispel more carbon dioxide. The cardiovascular system transports blood gases to and from the body tissues. The respiration system, through the breathing mechanism, performs the function of exchanging these gases with the external environment. Together, the cardiac and respiration systems form a larger anatomical and functional unit denoted the cardiopulmonary system.

Various disorders may affect the cardiovascular, respiratory, and other physiological systems. For example, heart failure (HF) is a clinical syndrome that impacts a number of physiological processes. Heart failure is an abnormality of cardiac function that causes cardiac output to fall below a level adequate to meet the metabolic demand of peripheral tissues. Heart failure is usually referred to as congestive heart failure (CHF) due to the accompanying venous and pulmonary congestion. Congestive heart failure may have a variety of underlying causes, including ischemic heart disease (coronary artery disease), hypertension (high blood pressure), and diabetes, among others.

There are a number of diseases and disorders that primarily affect respiration, but also impact other physiological systems. Emphysema and chronic bronchitis are grouped together and are known as chronic obstructive pulmonary disease (COPD). Pulmonary system disease also includes tuberculosis, sarcoidosis, lung cancer, occupation-related lung disease, bacterial and viral infections, and other diseases/disorders.

Normal breathing occurs when the central nervous system properly functions and sends signals instructing the body to breathe and obstructions to the airway are not present. Disordered breathing occurs when a patient experiences insufficient respiration with or without respiratory effort. Disordered breathing events may be classified by origin. For example, disordered breathing can originate from a deficiency in the central nervous system (central disordered breathing) or from an obstructed airway (obstructive disordered breathing).

Central disordered breathing is caused by a disruption of the nervous system signals that control breathing. During central disordered breathing events, the patient makes no effort to breath or the respiratory effort is insufficient.

Obstructive disordered breathing generally occurs due to an obstruction of a patient's airway. For example, the patient's tongue or other soft tissue of the throat may collapse into the patient's airway. The breathing reflex is triggered, the patient attempts to breathe, but respiration is disrupted because of the occluded airway. Disordered breathing events may involve central disordered breathing, obstructive disordered breathing, or a mixture of obstructive and central types of disordered breathing.

Although episodes of disordered breathing can occur when the patient is awake, they more often occur during sleep. Sleep apnea is characterized by periods of interrupted breathing during sleep. Hypopnea is another form of disordered breathing characterized by periods of shallow breathing. Sleep apnea, hypopnea and/or other forms of disordered breathing events may be associated with central, obstructive, or mixed disordered breathing origins. Other forms of disordered breathing that may be classified according to origin may include, for example, tachypnea (rapid breathing), hyperpnea (heavy breathing), dyspnea (labored breathing), and periodic breathing (periodically waxing and waning respiration).

A severe form of disordered breathing that generally includes periods of central sleep apnea is known as Cheyne-Stokes respiration (CSR). CSR is a type of periodic breathing marked by periodic patterns of waxing and waning respiration interrupted by periods of central apnea. CSR is commonly associated with poor prognosis when diagnosing congestive heart failure (CHF) patients.

Several mechanisms may be involved in central apneas observed in patients suffering from congestive heart failure. According to one mechanism, increased carbon dioxide sensitivity in CHF patients triggers hyperventilation initiating a sleep apnea episode. Breathing is regulated by a negative feedback system that maintains the arterial partial pressure of carbon dioxide ($PaCO_2$) within limits. Changes in $PaCO_2$ lead to changes in ventilation wherein the greater the sensitivity to carbon dioxide, the greater the ventilatory response.

In patients with increased sensitivity to carbon dioxide, the negative-feedback system that controls breathing initiates a large respiratory drive when $PaCO_2$ rises. The large respiratory drive produces hyperventilation. Hyperventilation, by driving the $PaCO_2$ level below the apneic threshold, results in central sleep apnea. As a result of the apnea, the $PaCO_2$ level rises again, leading to an increase in ventilation. In this way, cycles of hyperventilation and central apnea may recur throughout sleep.

There are a number of cardiovascular system disorders that have secondary effects with respect to other physiological systems. When functioning properly, the human heart maintains its own intrinsic rhythm, and is capable of pumping an adequate amount of blood throughout the body's circulatory system. However, some people have abnormal cardiac rhythms, referred to as cardiac arrhythmias, that cause a decrease in cardiac output.

Bradycardia is a disorder involving a heartbeat that is abnormally slow, causing insufficient blood supply to the body's tissues. Tachyarrhythmia occurs when the patient's cardiac rhythm is too fast. The excessively rapid cardiac contractions result in diminished blood circulation because the heart has insufficient time to fill with blood before contracting to expel the blood. Ventricular fibrillation is a particularly dangerous form of tachyarrhythmia, and may result in death within minutes if the heart's normal rhythm is not restored. Myocardial ischemia or infarction, caused by a lack of oxygen to heart tissues, promotes fibrillation. Because of the complex interactions between the cardiovascular, pulmonary and other systems, an effective approach to monitoring, diagnosis, and/or treatment of various disorders is needed.

SUMMARY OF THE INVENTION

Embodiments of the invention involve adapting gas therapy based on blood gas concentration. In accordance with one embodiment of the invention, a therapy method involves sensing concentration of a blood gas and adapting a gas therapy for a patient. The method further involves delivering the adapted gas therapy to the patient. At least one of sensing the blood gas concentration and adapting the gas therapy is performed at least in part implantably.

Other embodiments of methods in accordance with the present invention involve both sensing the blood gas concentration and adapting the therapy being performed at least in part implantably. Adapting a therapy may involve comparing the sensed blood gas concentration to a threshold and modifying the therapy if the blood gas concentration is beyond the threshold. Modifying the therapy may involve increasing or decreasing a gas pressure of a positive airway pressure device. Adapting a therapy may involve comparing the sensed blood gas concentration to a predetermined range and modifying the therapy if the blood gas concentration is beyond the predetermined range.

An embodiment of the present invention involves adapting oxygen therapy delivered to a patient, wherein adapting the therapy involves comparing a blood oxygen level to a predetermined range and modifying the therapy if the blood oxygen level is beyond a predetermined range, such as by increasing oxygen gas pressure in response to the blood oxygen level falling below a threshold. Alternatively, or additionally, adding or increasing a vasodilator or a bronchodilator in response to the blood oxygen level falling below a threshold may also be performed.

In accordance with another embodiment, a therapy system includes a sensor unit configured to sense blood gas concentration. A therapy controller is coupled to the sensor unit and is configured to adapt a gas therapy. The system further includes a gas therapy delivery unit coupled to the therapy controller and configured to deliver the adapted gas therapy to the patient. At least one of the sensor unit and the controller includes an implantable component.

Other embodiments in accordance with the present invention include each of the sensor unit and the therapy controller having an implantable component. The sensor unit may be a component of an implantable cardiac therapy device or a component of a patient-external respiratory therapy device. The sensor unit may include a blood oxygen sensor and/or carbon dioxide sensor, and may be coupled to an implantable cardiac therapy device, directly or wirelessly. In other embodiments, the sensor unit is coupled to the controller through the gas therapy delivery unit, which may deliver a vasodilating or a bronchodilator agent.

According to further embodiments, a sensor may be configured to detect disordered breathing, and, in response to detecting disordered breathing, gas therapy may be modified (e.g., initiated, modified, terminated) to suppress the disordered breathing. In addition, the type of disordered breathing may be discerned, such as discerning central apnea from obstructive apnea. If, for example, central apnea is detected, small amounts of carbon dioxide may be applied to the patient's air supply (e.g., via a positive airway pressure device) to mitigate the carbon dioxide instability that is leading to central apnea.

BRIEF DESCRIPTION OF THE DRAWINGS

FIG. 12 is a block diagram of a medical system that may be used to implement coordinated patient monitoring, diagnosis, and/or therapy in accordance with embodiments of the present invention.

Figure 1:
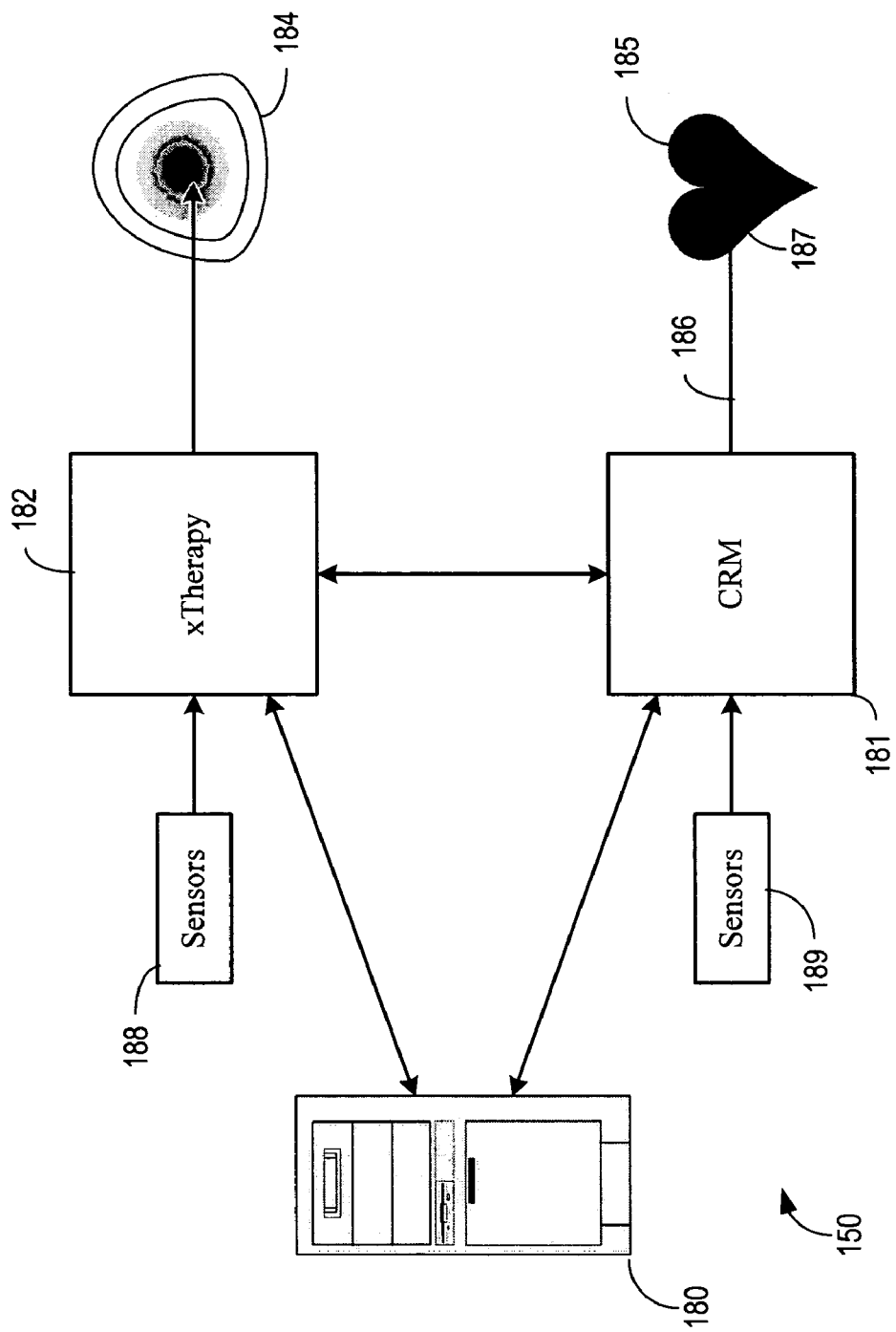
FIG. 1 is a block diagram of a system that provides and adjusts a gas therapy by cooperation between internal and external medical devices in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which are shown by way of illustration, various embodiments by which the invention may be practiced. It is to be understood that other embodiments may be utilized, and structural and functional changes may be made without departing from the scope of the present invention.

Disorders and diseases affecting the interdependent physiological systems of the human body may be more effectively diagnosed and treated using a coordinated approach. Various embodiments of the present invention are implemented using medical systems employing one or a number of patient-external and/or patient-internal medical devices. Medical devices may communicate or otherwise operate in concert or in a stand-alone manner to provide more comprehensive patient monitoring, diagnosis, and therapy.

Many patients suffering from obstructive sleep apnea (OSA) have intermittent oxygen desaturation associated with periods of apnea or hypopnea. Oxygen saturation levels below 90% are considered harmful. Usually, treatment is directed at correcting the apnea, which may in turn prevent hypoxemia. Unfortunately, many patients do not tolerate nasal continuous positive airway pressure (CPAP) therapy or are not candidates for surgical correction of their OSA. For these patients, oxygen administration for the correction of OSA-related nocturnal hypoxemia may reduce symptoms of OSA. Carbon dioxide therapy has also been successfully used to treat central apneas as well, including Cheyne-Stokes respiration (CSR). In accordance with embodiments of the invention, a system controls gas therapy using one or more patient-internal sensors, one or more patient-external sensors, and/or an implanted device.

Gas therapy, such as oxygen or carbon dioxide therapy, continuous positive airway pressure therapy, or other therapies provided to a patient through the pulmonary system, may mitigate a patient's suffering from a number of respiratory disorders. Some lung diseases, such as emphysema, sarcoidosis, and chronic obstructive pulmonary disorder, reduce lung function to the extent that supplemental oxygen is needed to continue normal bodily functions. For many patients with end stage lung disease, oxygen therapy allows the patients to get the oxygen they need, helps them be more active, and may also prevent heart failure.

Gas therapy devices may be used to provide a variety of respiration therapies, including, for example, providing vasodilating or bronchodilator agents, continuous positive airway pressure (CPAP), bi-level positive airway pressure (bi-level PAP), proportional positive airway pressure (PPAP), auto-titrating positive airway pressure, ventilation, oxygen, carbon dioxide or other gas therapies. All types of gas therapy and positive airway pressure devices are referred to generically herein as xTherapy devices.

The following discussion, with reference to FIGS. 1 through 5, describes embodiments of the invention involving modulation of external gas therapy. The processes and systems exemplified by these embodiments may be implemented alone or in combination with one or more processes and systems exemplified by other embodiments described herein to provide a coordinated approach to patient monitoring, diagnosis, and/or therapy.

In accordance with embodiments of the invention, a system controls gas therapy, such as oxygen or carbon dioxide therapy, using one or more patient-internal sensors, one or more patient-external sensors and/or an implanted device. The gas therapy may be delivered to the patient, and measurement of exhaled gas concentration may be implemented using a respiratory mask, such as a CPAP mask, for example. The one or more sensors may include, for example, a gas saturation sensor or other implanted sensor for determining the patient's blood gas saturation. Other sensors, such as a disordered breathing detector (internal or external) may be used to determine the presence of disordered breathing, and then deliver gas therapy as needed to resolve or treat the disordered breathing. The patient's blood gas saturation may be determined externally, e.g., using pulse oximetry techniques, and/or external sensors positioned on a respiratory mask or nasal cannulae.

One illustrative approach involves sensing the patient's blood gas saturation and controlling the delivery of gas by a patient-external therapy device based on the blood gas saturation. At least one of sensing the blood gas saturation and controlling the delivery of gas is performed at least in part implantably.

Another approach involves sensing the body's need for gas, as manifested, for example, as apnea, hypopnea, hypoxia, hypocapnia, or myocardial ischemia, and then providing appropriate gas therapy to remedy the physiological need. Sensing of the body's need for gas may be effected either internally or externally of the patient.

As referenced herein, the term "condition" denotes a parameter that may be sensed, measured, and/or otherwise discerned based on a signal generated by a sensor or other input device of the one or more medical devices. For example, a physiological sensor typically generates a signal modulated by a particular physiological parameter. In some cases, a physiological condition, as the term is used herein, may be directly measured based on the sensor signal. In other cases, a physiological condition measurement may be derived from the sensor signal.

The terms "symptom" and "physiological change" refer to a manifestation of a medical disease or disorder. Symptoms and/or physiological changes may be detectable based on a sensed presence of one or more physiological conditions and/or measured values associated with the one or more sensed physiological conditions. The terms "disease" and/or "disorder" are used to refer to a medical dysfunction that is characterizable by a collection of symptoms or physiological changes.

FIG. 1 illustrates a block diagram of a system 150 for providing coordinated cardiac and respiratory therapy in accordance with embodiments of the invention. The system utilizes an xTherapy device 182 to provide respiratory therapy to the patient. A controlled flow of air, oxygen, carbon dioxide or other gas is developed by the xTherapy device 182 and delivered to the patient's airway through tubing and a mask 184, such as a nasal mask.

The system 150 provides electrical stimulation therapy using an implantable cardiac rhythm management (CRM) device 181. The CRM device 181 provides electrical stimulation to the heart 185 through an implanted lead system 186 with electrodes 187 positioned in, on, or about the heart 185 to electrically couple the heart 185 to the CRM device 181. The CRM device 181 may be used to sense symptoms of a disease or disorder, such as hypoxemia and ischemia. The CRM device 181 may also be used to improve cardiac output by atrial pacing, bi-ventricular pacing, atrial or ventricular overdrive pacing, pacing above a programmed pacing rate, and/or other therapies, which may, in turn, improve blood gas transport.

One or both of the xTherapy device 182 and the CRM device 181 have one or more sensors 188, 189 for sensing conditions associated with disordered breathing. For example, the CRM sensors 189 may include, for example, cardiac signal electrodes, a minute ventilation (MV) sensor, and an accelerometer. The xTherapy device sensors 188 may include a microphone and respiratory flow sensor.

The sensor signals are analyzed by the xTherapy device 182, the CRM device 181, or both devices 182, 181, to determine the presence and/or severity of a disorders such as ischemia, hypoxemia, pulmonary, and/or disordered breathing. The xTherapy and CRM devices 182, 181 may have bi-directional or unidirectional communication capability for communicating information about the disordered breathing to the other device 181, 182. In one scenario, the xTherapy 182 and the CRM 181 have the ability to communicate directly, e.g., through a wireless link. In another scenario, the xTherapy 182 and the CRM 181 do not have the ability to communicate directly, but communicate through an intermediate device 180, such as a programmer or an information server 180 used in connection with an advanced patient management system. The intermediary device 180 may receive information from the xTherapy device 182 and transmit the information to the CRM device 181. Similarly, the intermediary device 180 may receive information from the CRM device 181 and transmit the information to the xTherapy device 182.

In one example, either the CRM device 181 or the xTherapy device 182 may sense a set of patient conditions and transmit the patient conditions to the other device 182, 181. For example, the CRM device 181 may sense a set of patient conditions using the sensors 189 coupled to the CRM device 181. The CRM device 181 may then transmit the sensor information to the xTherapy device 182. Each device 181, 182 may individually detect a disorder such as ischemia, hypoxemia, pulmonary, and/or disordered breathing and determine the severity of the disorder based on the sensor information. Each device 181, 182 may adjust the therapy provided by the device based on the detection and/or severity of the detected disorder.

In another example, the xtherapy device 182 may sense a set of patient conditions and transmit the patient conditions to the CRM device 181. The xTherapy device 182 and the CRM device 181 may individually modify their therapies based on the sensed conditions.

In yet another example the xTherapy device 182 may sense a first set of patient conditions and transmit the first set of patient conditions to the CRM device 181. The CRM device 181 may detect a second set of patient conditions and transmit the second set of patient conditions to the xTherapy device 182. The xTherapy and CRM devices 182, 181 may then individually modify their therapies based on the first and the second sets of conditions.

In another example, the detection and/or determination of the severity of a disorder, such as ischemia, hypoxemia, pulmonary, and/or disordered breathing, may be performed in one device and the information transmitted to the other device. For example, the CRM device 181 may sense a first set of patient conditions from sensors 189 coupled to the CRM device 181 and receive a second set of patient conditions from the xTherapy device 182. The CRM device 181 may detect a disorder such as ischemia, hypoxemia, pulmonary, and/or disordered breathing and determine the severity of the disorder based on the first and the second set of conditions. The CRM device 181 may transmit information about the detection/severity of a condition such as ischemia, hypoxemia, pulmonary, and/or disordered breathing to the xTherapy device 182. The CRM device 181 may modify its therapy based on the detection/severity of the disorder. The xtherapy device 182 may also modify its therapy based on the detection/severity of the disorder. In an alternate embodiment, the detection and severity determination may be performed by the xTherapy device 182 and transmitted to the CRM device 181.

Therapy provided by the xTherapy device 182 may include, for example, therapy delivery at a variable pressure, e.g., autotitration PAP, gas therapy, among others. Therapy provided by the CRM device 181 may include, for example, cardiac resynchronization therapy, bi-ventricular pacing, atrial or ventricular overdrive pacing, and/or pacing above a programmed sleep rate.

The detection of a disorder such as ischemia, hypoxemia, pulmonary, and/or disordered breathing and determination of the severity of the disorder may be used to implement an adaptive therapy utilizing both the xTherapy device 182 and the CRM device 181. The adaptive therapy techniques described above may be used in connection with the xTherapy device 182 alone or with the CRM and xTherapy devices 181, 182 together. Thus, the therapy provided by either or both devices 181, 182 may be initiated, terminated, or modified based on the effectiveness of the therapy, the impact of the therapy on the patient, or both effectiveness and impact.

Figure 2:
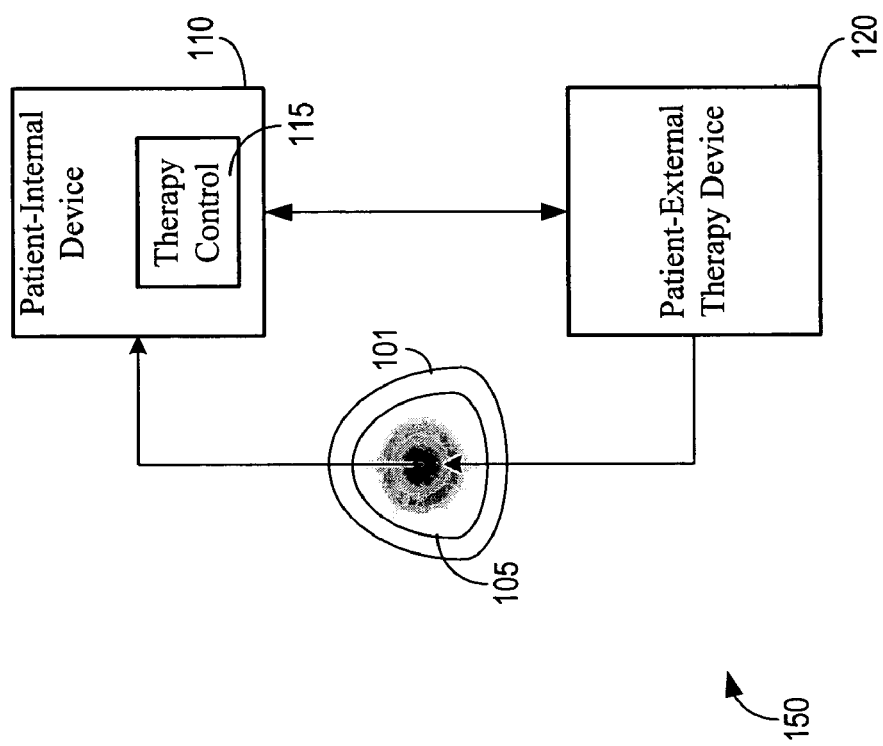
FIG. 2 is a block diagram illustrating a system for modulating a patient-external therapy device in combination with a patient-internal device incorporating therapy control in accordance with embodiments of the present invention.

FIG. 2 illustrates the use of one or more external sensors with the patient-internal device operating as the gas therapy control unit in accordance with embodiments of the invention. A patient-external therapy device 120 provides gas therapy to a patient, for example, through a nasal or facial mask 101. In this example, the therapy control unit 115, located in a patient-internal device 110, such as a CRM device, receives blood gas information from an external sensor 105, such as, but not limited to, a sensor positioned on a respiratory mask. It is understood that other sensors may be used which are not positioned on a respiratory mask, such as a finger oximetry sensor. The sensor 105 may communicate with the patient-internal device 110 through, for example, a wireless communication link.

Alternatively, the sensor signals may be received by the patient-external therapy device 120, e.g., CPAP device or other xTherapy device, and transmitted from the patient-external device 120 to the patient-internal device 110, for example. The therapy control unit 115 compares the sensed gas saturation level to a predetermined threshold or range. When the gas saturation is beyond the threshold or range, the patient-internal device 110 may transmit control signals to the patient-external therapy delivery device 120 to initiate, terminate, or modify the gas therapy.

Figure 3:
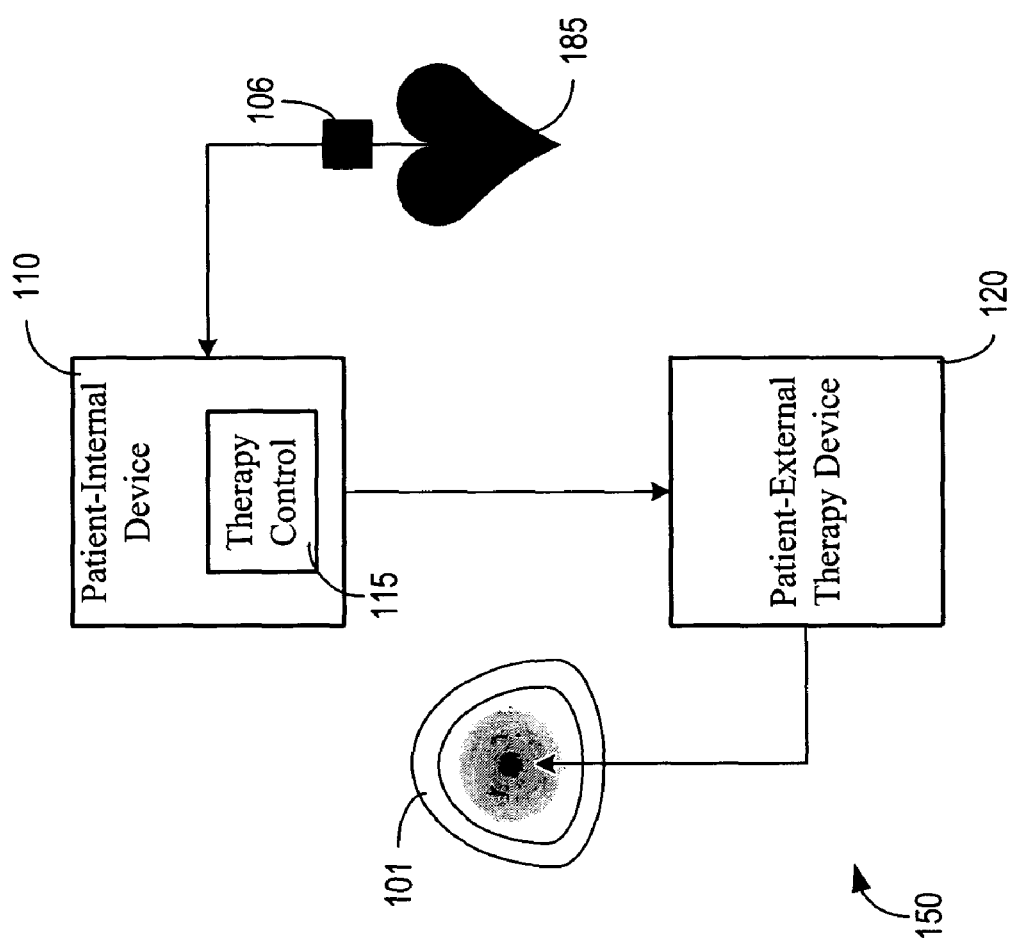
FIG. 3 is a block diagram illustrating a system for modulating a patient-external therapy device with a sensor in a respiratory mask in combination with a patient-internal device incorporating therapy control in accordance with embodiments of the present invention.

FIG. 3 illustrates another implementation of gas therapy control in accordance with an embodiment of the invention. In the example depicted in FIG. 3, gas saturation is sensed using one or more patient-internal sensors 106 positioned on an endocardial lead. In this implementation, the patient-internal sensors 106 may include a gas saturation sensing lead used with an implantable CRM device. The gas sensing device need not be positioned on a lead, but may alternatively be located on the CRM device housing or header, or on a sensor lead independent from the pacing leads. The patient-internal device 110 includes a gas therapy control unit 115. In this example, the therapy control unit 115 receives blood gas information from the blood gas sensor 106. The therapy control unit 115 compares the sensed gas saturation level to a predetermined threshold or range. When the gas saturation is beyond the threshold or range, the patient-internal device 110 may transmit control signals to the patient-external therapy delivery device 120 to initiate, terminate, or modify the gas therapy.

Figure 4:
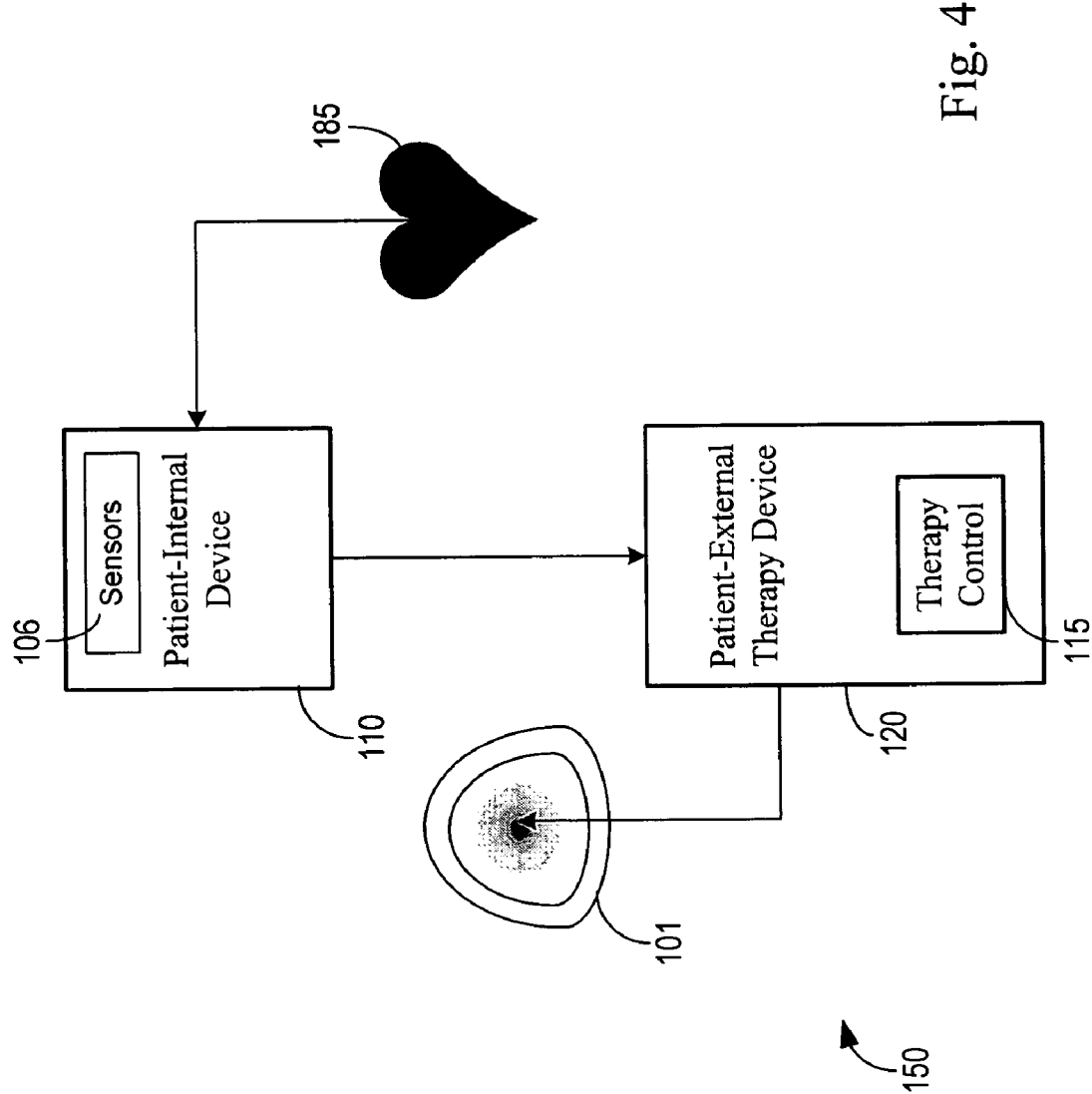
FIG. 4 is a block diagram illustrating a system for modulating a patient-external therapy device incorporating therapy control in combination with a patient-internal device configured to transmit information to the external device in accordance with embodiments of the present invention.

FIG. 4 illustrates another implementation of gas therapy control in accordance with an embodiment of the invention. In the example depicted in FIG. 4, gas saturation is sensed using one or more patient-internal sensors 106 positioned in or on the patient-internal device 110, such as the can of a cardiac monitoring and/or stimulation device. In this implementation, the patient-internal sensors 106 may include a gas saturation sensing lead used with an implantable CRM device. The patient-external device 120 includes a gas therapy control unit 115. In this example, the therapy control unit 115 receives blood gas information from the blood gas sensor 106 via, for example, wireless link. The therapy control unit 115 compares the sensed gas saturation level to a predetermined threshold or range. When the gas saturation is beyond the threshold or range, the patient-external device 120 may initiate, terminate, or modify the gas therapy.

Figure 5:
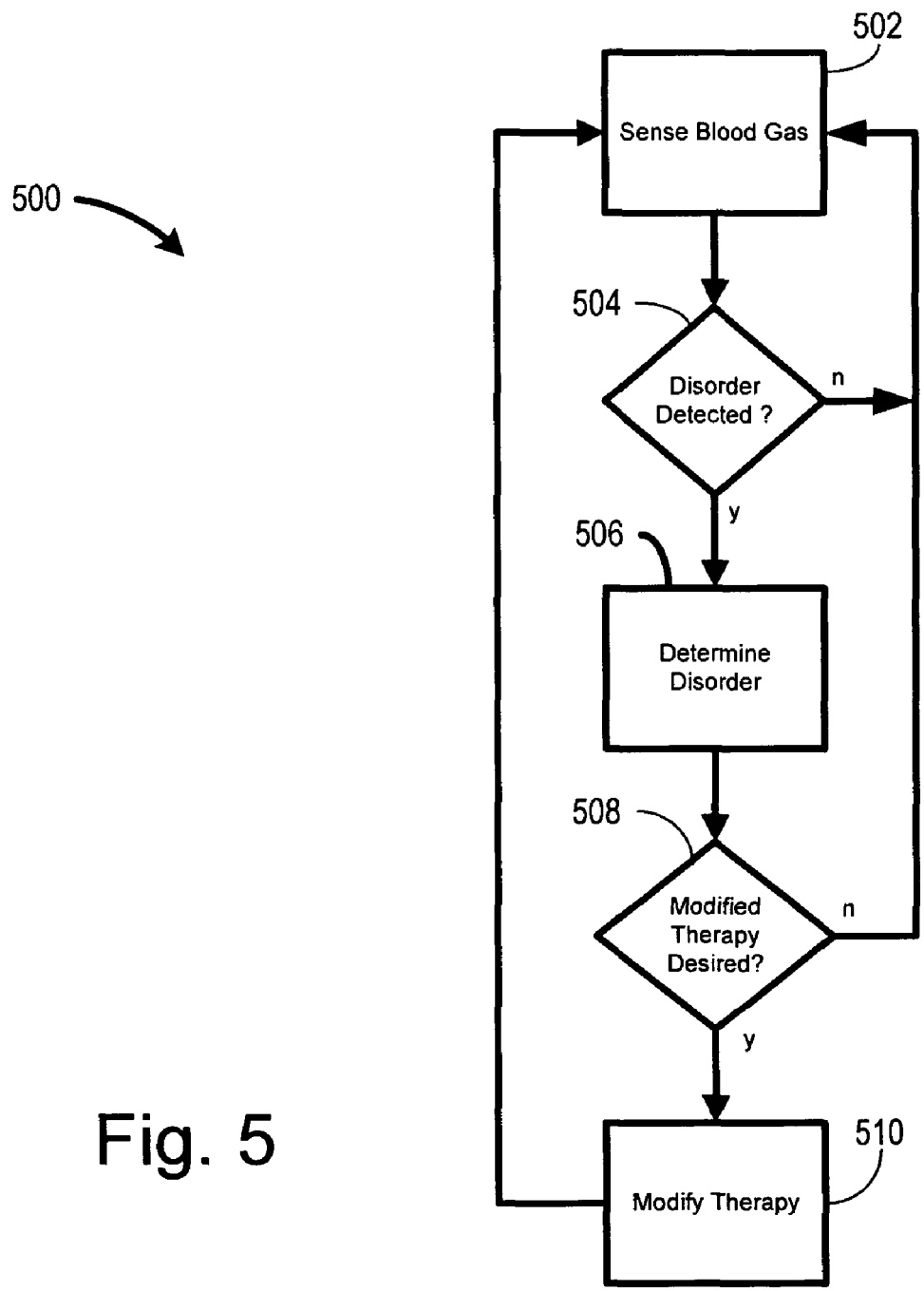
FIG. 5 is a flow chart illustrating a method of gas therapy control based on signals transmitted from a patient-internal device in accordance with embodiments of the present invention.

FIG. 5 is a flow chart illustrating a method 500 of gas therapy control based on signals from a patient-internal device in accordance with embodiments of the present invention. The method 500 may be useful for controlling any gas therapy system, such as those illustrated with reference to FIGS. 1 through 4. For clarity of understanding, and not by way of limitation, the sensing of blood oxygen level will be used as an example of one particular use of the method 500.

Block 502 provides for the sensing of blood gas, such as blood oxygen level. A disorder is detected 504 using the sensed blood gas information. For example, a blood oxygen level may be compared to a range of acceptable blood oxygen levels to detect whether the blood gas is within an acceptable range, or whether some disorder is indicated. If no disorder is detected at block 504, blood gas sensing continues at block 502. Sensing may occur continuously, intermittently, by-request, periodically, or as otherwise desired or needed.

If a disorder is detected at detection block 504, a determination of one or more possible actions and/or interventions is made at block 506, relative to the detected disorder. For example, detecting a blood oxygen level below a lower threshold may suggest that more oxygen is needed by the patient. A decision is made at block 508, based on the determination from block 506, as to whether therapy initiation or therapy modification is desired to increase the patient's blood oxygen level. For example, if a patient is receiving oxygen therapy, the oxygen level administered to the patient may be increased. In another embodiment, if the patient is sleeping and wearing a CPAP device, the air pressure may be increased. In a further embodiment, the patient may be administered a vasodilating or bronchodilator agent, or have a level of vasodilating or bronchodilator agent therapy modified. Combined therapies may also be performed, such as increasing gas pressure and adding a vasodilating or bronchodilator agent, increasing the heart rate of a patient using a pacemaker and increasing oxygen therapy, or other desired combined therapies.

If no therapy change is desired, the disorder may be recorded, monitored, or alerted, for example, before returning to the sense block 502. If a therapy change is desired, the therapy is modified at block 510 before again returning to the blood sense block 502. For example, if a patient is receiving oxygen therapy, the oxygen level administered to the patient is increased, and the method 500 may be performed again after an appropriate time to determine if the change was effective, or whether other action is necessary.

Figure 6:
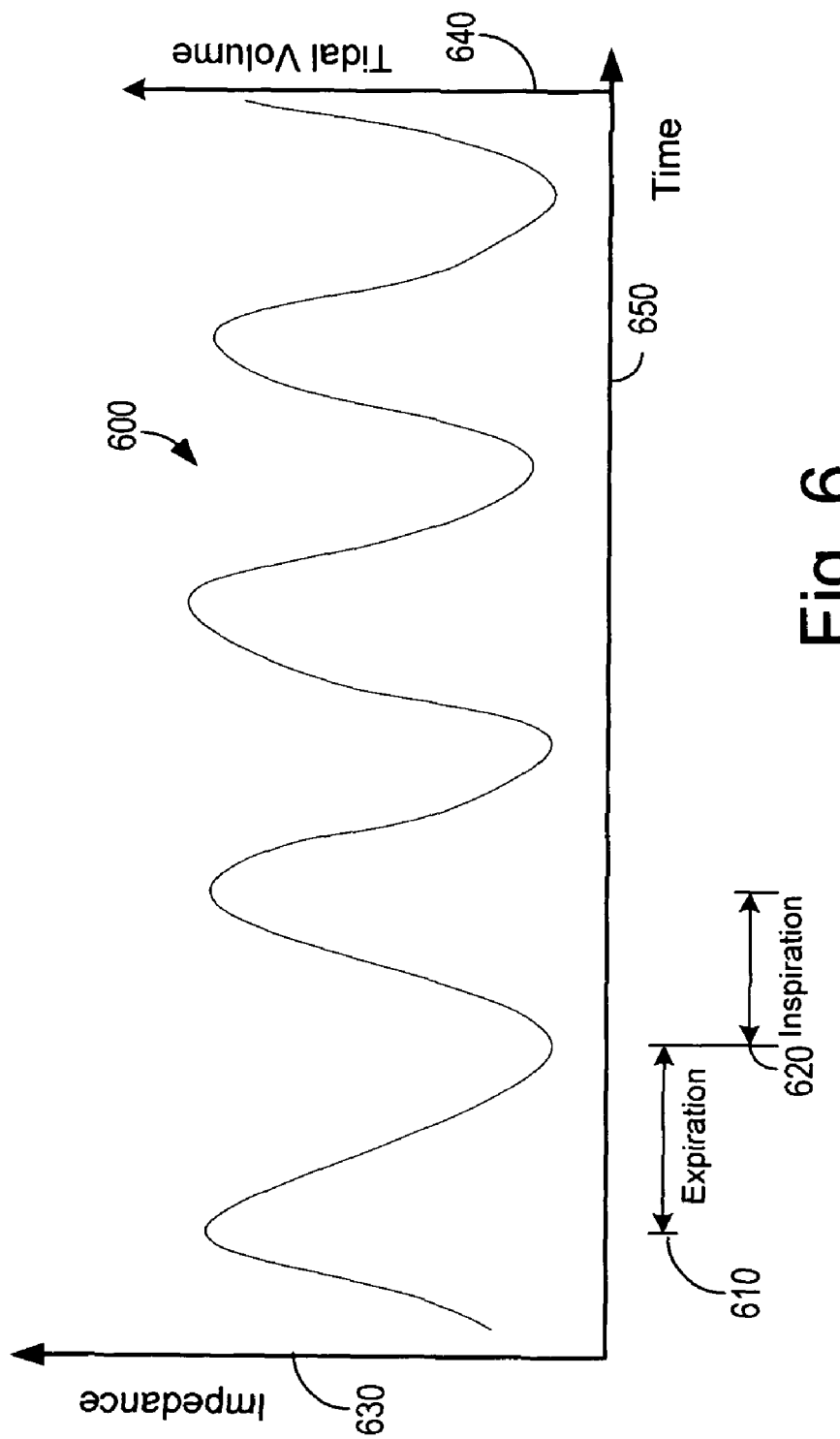
FIG. 6 is a graph of a normal respiration signal measured by a transthoracic impedance sensor that may be utilized for coordinated monitoring, diagnosis, and/or therapy in accordance with embodiments of the present invention.

Referring now to FIG. 6, an impedance signal 600 is illustrated. The impedance signal 600 may be developed, for example, from an impedance sense electrode in combination with a CRM device. The impedance signal 600 is proportional to the transthoracic impedance, illustrated as an impedance 630 on the abscissa of the left side of the graph in FIG. 6.

The impedance 630 increases during any respiratory inspiration 620 and decreases during any respiratory expiration 610. The impedance signal 600 is also proportional to the amount of air inhaled, denoted by a tidal volume 640, illustrated on the abscissa of the right side of the graph in FIG. 6. The variations in impedance during respiration, identifiable as the peak-to-peak variation of the impedance signal 600, may be used to determine the respiration tidal volume 640. Tidal volume 640 corresponds to the volume of air moved in a breath, one cycle of expiration 610 and inspiration 620. A minute ventilation may also be determined, corresponding to the amount of air moved per one minute of time 650 illustrated on the ordinate of the graph in FIG. 6.

Arousal and other episodes of breathing disorders may be determined using the impedance signal 600. During non-REM sleep, a normal respiration pattern includes regular, rhythmic inspiration-expiration cycles without substantial interruptions. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 7:
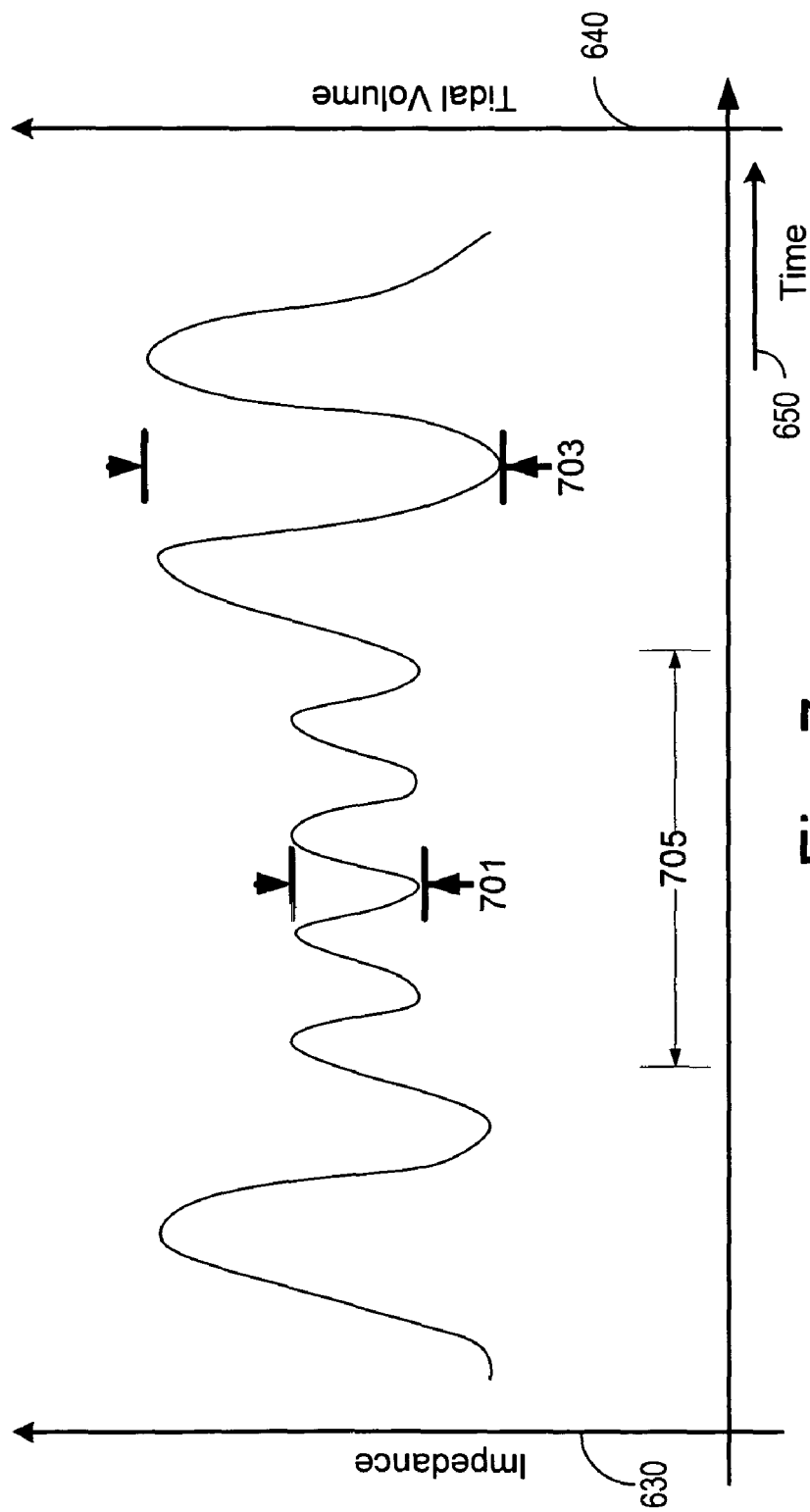
FIG. 7 is a respiration graph illustrating abnormally shallow respiration utilized in detection of disordered breathing in accordance with embodiments of the present invention.

Hypopnea is a form of disordered breathing characterized by abnormally shallow breathing. FIG. 7 is a graph of tidal volume derived from transthoracic impedance measurements. The graph of FIG. 7 illustrating the tidal volume of a hypopnea episode may be compared to the tidal volume of a normal breathing cycle illustrated previously in FIG. 6, which illustrated normal respiration tidal volume and rate. As shown in FIG. 7, hypopnea involves a period of abnormally shallow respiration, possible at an increased respiration rate.

Hypopnea is detected by comparing a patient's respiratory tidal volume 703 to a hypopnea tidal volume 701. The tidal volume for each respiration cycle may be derived from transthoracic impedance measurements acquired in the manner described previously. The hypopnea tidal volume threshold may be established by, for example, using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

In FIG. 7, a hypopnea episode 705 is identified when the average tidal volume is significantly below the normal tidal volume. In the example illustrated in FIG. 7, the normal tidal volume during the breathing process is identified as the peak-to peak value identified as the respiratory tidal volume 703. The hypopnea tidal volume during the hypopnea episode 705 is identified as hypopnea tidal volume 701. For example, the hypopnea tidal volume 701 may be about 50% of the respiratory tidal volume 703.

The value 50% is used by way of example only, and determination of thresholds for hypopnea events may be determined as any value appropriate for a given patient. In the example above, if the tidal volume falls below 50% of the respiratory tidal volume 703, the breathing episode may be identified as a hypopnea event, originating the measurement of the hypopnea episode 705.

Figure 8:
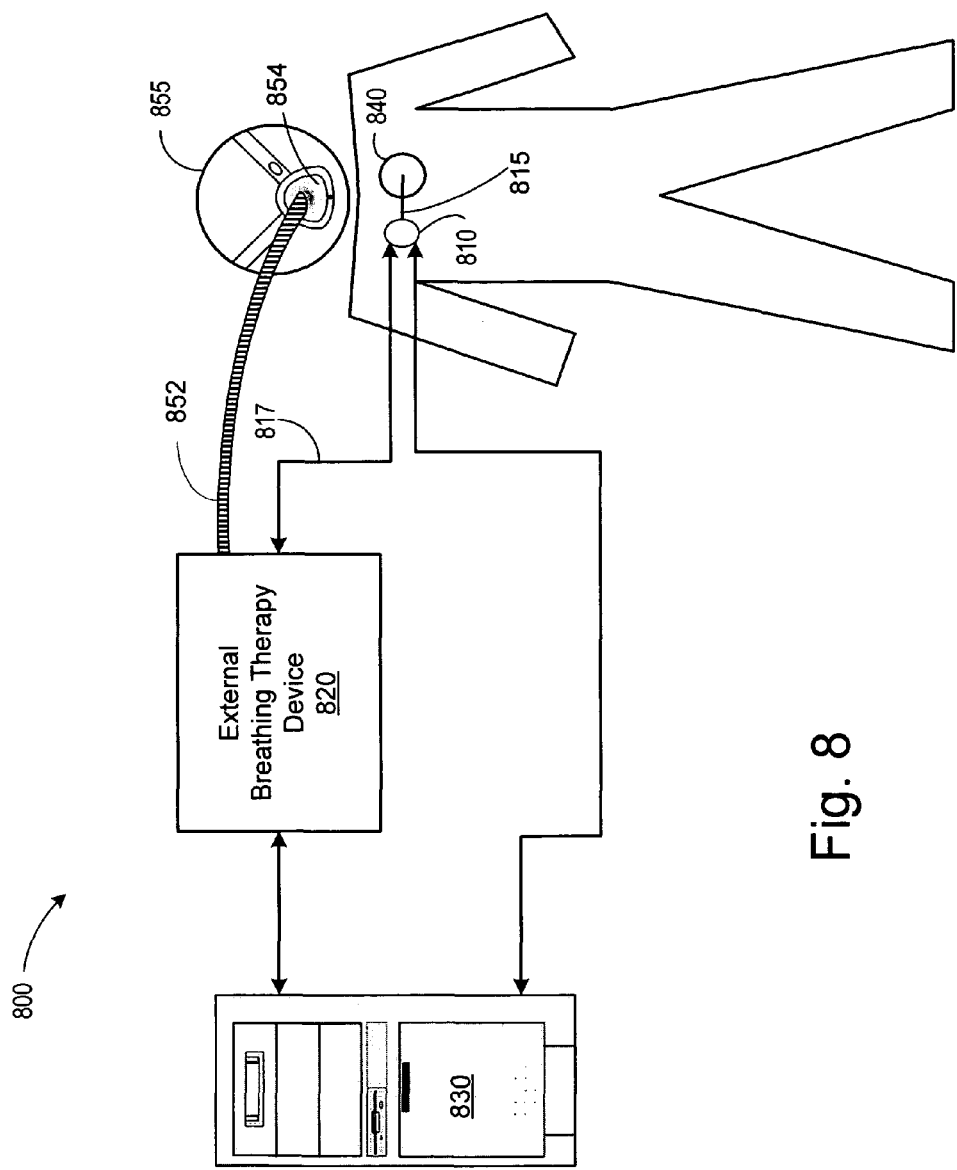
FIG. 8 illustrates a medical system including an implantable cardiac rhythm management device that cooperates with a patient-external respiration therapy device to provide coordinated patient monitoring, diagnosis and/or therapy in accordance with an embodiment of the present invention.

According to one embodiment of the present invention, illustrated in FIG. 8, a medical system 800 may include an implantable CRM 810 that cooperates with an xTherapy device 820 to provide coordinated patient monitoring, diagnosis and/or therapy. The CRM 810 may provide a first set of monitoring, diagnostic, and/or therapeutic functions to a patient 855. The CRM 810 may be electrically coupled to a patient's heart 840 through one or more cardiac electrodes 815 terminating in, on, or about the heart 840. The cardiac electrodes 815 may sense cardiac signals produced by the heart 840 and/or provide therapy to one or more heart chambers. For example, the cardiac electrodes 815 may deliver electrical stimulation to one or more heart 840 chambers, and/or to one or multiple sites within the heart 840 chambers. The CRM 810 may directly control delivery of one or more cardiac therapies, such as cardiac pacing, defibrillation, cardioversion, cardiac resynchronization, and/or other cardiac therapies, for example. In addition, the CRM 810 may facilitate the control of the xtherapy device 820. Further, the CRM 810 may perform various monitoring and/or diagnostic functions in relation to the cardiovascular system and/or other physiological systems.

In the example illustrated in FIG. 8, a mechanical respiration therapy device, such as the patient-external respiration therapy device 820, includes a positive airway pressure device that cooperates with the CRM 810. The xTherapy device 820 develops a positive air pressure that is delivered to the patient's airway through a tube system 852 and a mask 854 connected to the xTherapy device 820. Positive airway pressure devices are often used to treat disordered breathing. In one configuration, for example, the positive airway pressure provided by the xTherapy device 820 acts as a pneumatic splint keeping the patient's airway open and reducing the severity and/or number of occurrences of disordered breathing due to airway obstruction.

The xTherapy device 820 may directly control the delivery of respiration therapy to the patient, and may contribute to the control of the CRM device 810. In addition, the xTherapy device 820 may provide a number of monitoring and/or diagnostic functions in relation to the respiratory system and/or other physiological systems.

The CRM 810 and xTherapy device 820 may communicate directly through a wireless communications link 817, for example. Alternatively, or additionally, the CRM 810 and xTherapy device 820 may communicate with and/or through an APM such as the APM system 830, as may be described further below with reference to FIG. 12.

Although FIG. 8 illustrates a CRM device 810 used with an xTherapy device 820 to provide coordinated patient monitoring, diagnosis and/or therapy, any number of patient-internal and patient-external medical devices may be included in a medical system in accordance with the present invention. For example, a drug delivery device, such as a drug pump or controllable nebulizer, may be included in the system 800. The drug delivery device may cooperate with either or both of the CRM device 810 and the xTherapy device 820 and may contribute to the patient monitoring, diagnosis, and/or therapeutic functions of the medical system 800.

Figure 9:
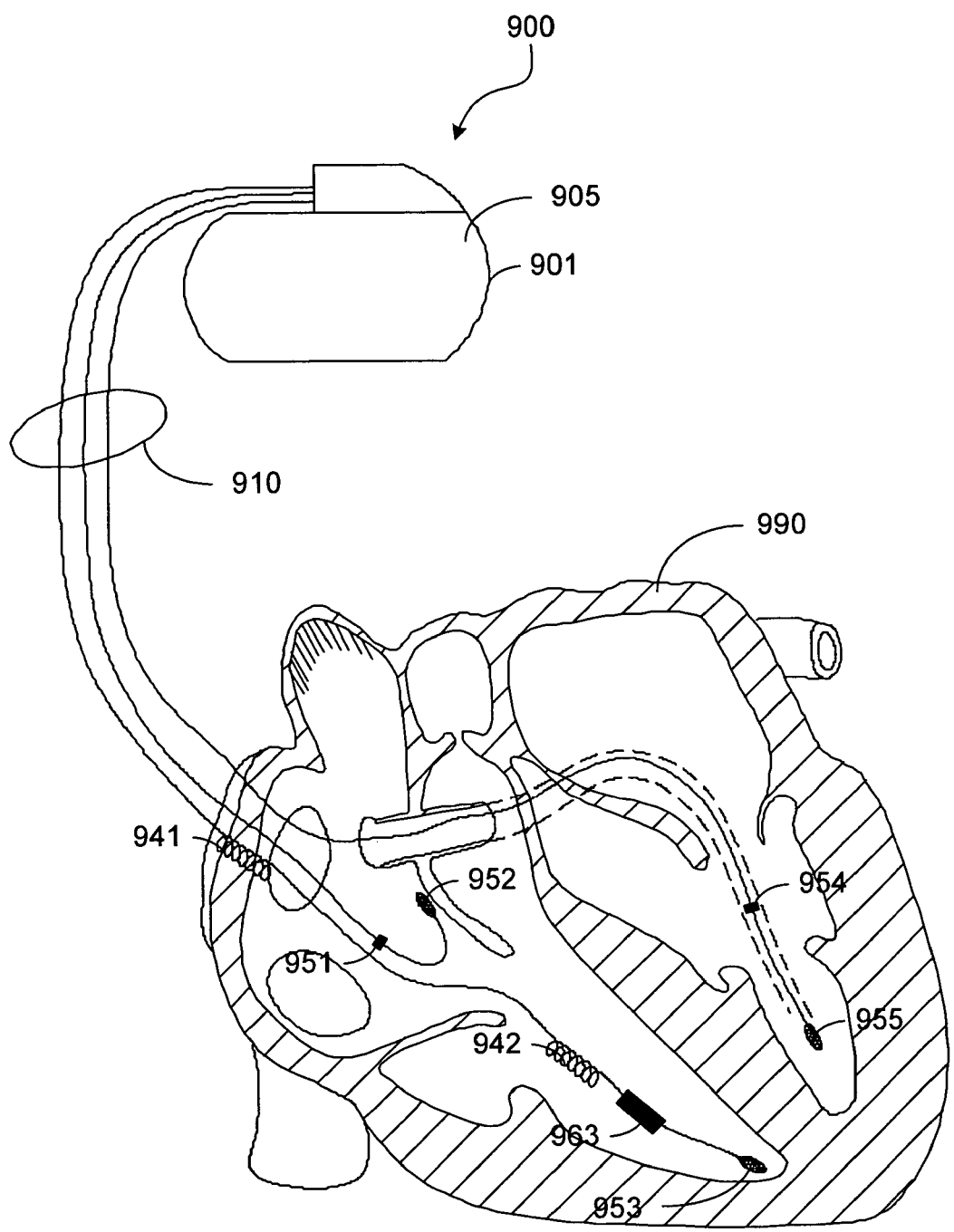
FIG. 9 is an illustration of an implantable cardiac device including a lead assembly shown implanted in a sectional view of a heart, the device used for coordinated patient monitoring, diagnosis, and/or therapy in accordance with embodiments of the present invention.

FIG. 9 is a partial view of an implantable device useful for providing sensing and/or therapy in accordance with embodiments of the invention. In this example, the implantable device comprises a cardiac rhythm management device (CRM) 900 including an implantable pulse generator 905 electrically and physically coupled to an intracardiac lead system 910. Portions of the intracardiac lead system 910 are inserted into the patient's heart 990. The intracardiac lead system 910 includes one or more electrodes configured to sense electrical cardiac activity of the heart, deliver electrical stimulation to the heart, sense the patient's transthoracic impedance, and/or sense other physiological parameters, e,g, cardiac chamber pressure or temperature. Portions of the housing 901 of the pulse generator 905 may optionally serve as a can electrode.

Communications circuitry is disposed within the housing 901 for facilitating communication between the pulse generator 905 and an external communication device, such as a portable or bed-side communication station, patient-carried/ worn communication station, or external programmer, for example. The communications circuitry can also facilitate unidirectional or bidirectional communication with one or more implanted, external, cutaneous, or subcutaneous physiologic or non-physiologic sensors, patient-input devices and/ or information systems.

The pulse generator 905 may optionally incorporate a motion detector that may be used to sense various respiration-related conditions. For example, the motion detector may be optionally configured to sense snoring, activity level, and/or chest wall movements associated with respiratory effort, for example. The motion detector may be implemented as an accelerometer positioned in or on the housing 901 of the pulse generator 905. If the motion sensor is implemented as an accelerometer, the motion sensor may also provide respiratory, e.g. rales, coughing, and cardiac, e.g. S1-S4 heart sounds, murmurs, and other acoustic information.

The lead system 910 of the CRM 500 may incorporate one or more transthoracic impedance sensors that may be used to acquire the patient's respiration waveform, or other respiration-related information. The transthoracic impedance sensor may include, for example, one or more intracardiac electrodes 941, 942, 951-955, 963 positioned in one or more chambers of the heart 990. The intracardiac electrodes 941, 942, 951-955, 963 may be coupled to impedance drive/sense circuitry positioned within the housing of the pulse generator 905.

In one implementation, impedance drive/sense circuitry generates a current that flows through the tissue between an impedance drive electrode 951 and a can electrode on the housing 901 of the pulse generator 905. The voltage at an impedance sense electrode 952 relative to the can electrode changes as the patient's transthoracic impedance changes. The voltage signal developed between the impedance sense electrode 952 and the can electrode is detected by the impedance sense circuitry. Other locations and/or combinations of impedance sense and drive electrodes are also possible.

The voltage signal developed at the impedance sense electrode 952 is proportional to the patient's transthoracic impedance and represents the patient's respiration waveform. The transthoracic impedance increases during respiratory inspiration and decreases during respiratory expiration. The peak-to-peak transition of the transthoracic impedance is proportional to the amount of air moved in one breath, denoted the tidal volume. The amount of air moved per minute is denoted the minute ventilation. A normal "at rest" respiration pattern, e.g., during non-REM sleep, includes regular, rhythmic inspiration-expiration cycles without substantial interruptions.

The lead system 910 may include one or more cardiac pace/sense electrodes 951-955 positioned in, on, or about one or more heart chambers for sensing electrical signals from the patient's heart 990 and/or delivering pacing pulses to the heart 990. The intracardiac sense/pace electrodes 951-955, such as those illustrated in FIG. 9, may be used to sense and/or pace one or more chambers of the heart, including the left ventricle, the right ventricle, the left atrium and/or the right atrium. The lead system 910 may include one or more defibrillation electrodes 941, 942 for delivering defibrillation/cardioversion shocks to the heart. The pulse generator 905 may include circuitry for detecting cardiac arrhythmias and/or for controlling pacing or defibrillation therapy in the form of electrical stimulation pulses or shocks delivered to the heart through the lead system 910 to treat the detected arrhythmias.

Figure 10:
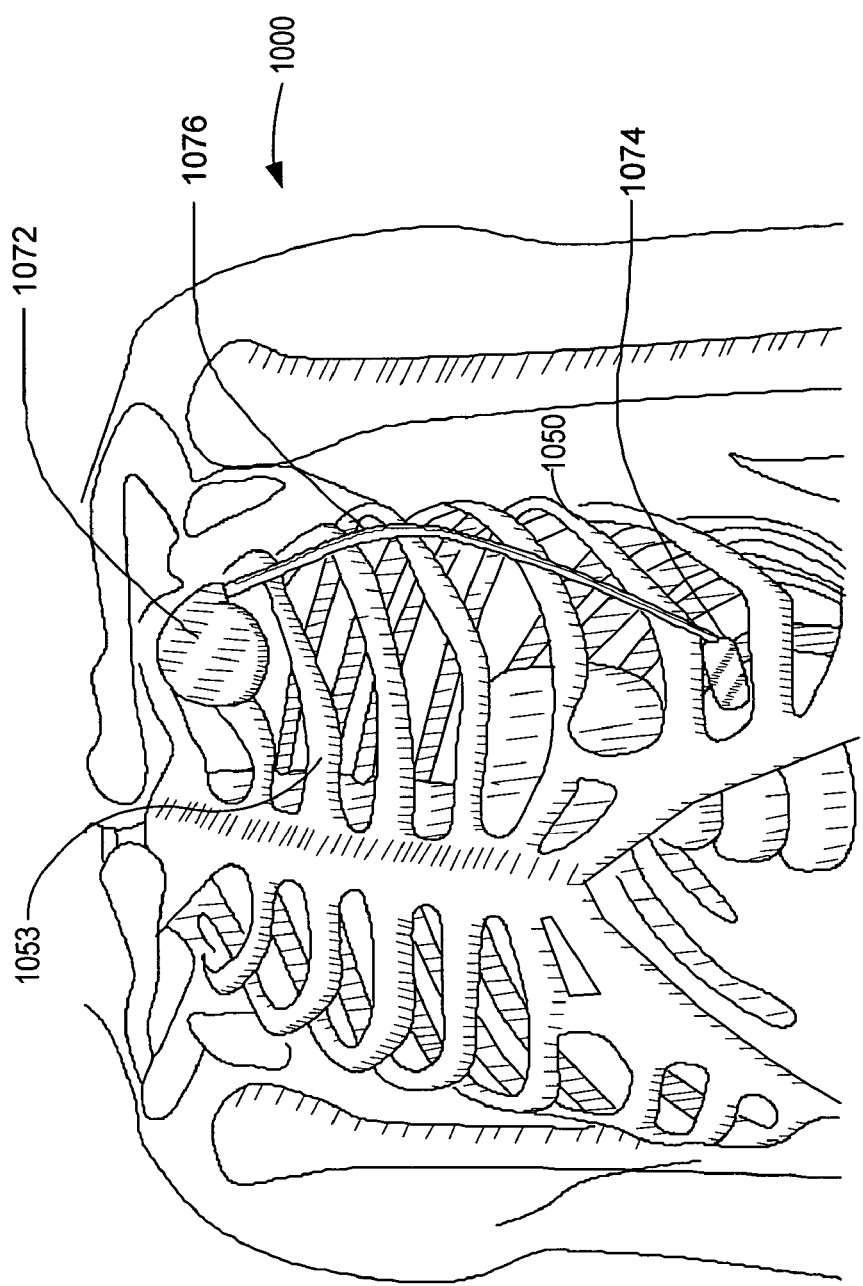
FIG. 10 is an illustration of a thorax having an implanted subcutaneous medical device that may be used for coordinated patient monitoring, diagnosis, and/or therapy in accordance with an embodiment of the present invention.

FIG. 10 is a diagram illustrating a subcutaneous implantable medical device 1000 that may be used for gas therapy systems incorporating an implantable component in accordance with embodiments of the present invention. The device 1000 illustrated in FIG. 10 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of a rib cage 1050 at an intercostal or subcostal location, within the abdomen, or in the upper chest region (e.g., subclavian location, such as above a third rib 1053). In one implementation, one or more electrodes may be located on a primary housing 1072 and/or at other locations about, but not in direct contact with the heart, great vessel or coronary vasculature.

In another implementation, one or more electrodes may be located in direct contact with the heart, great vessel or coronary vasculature, such as via one or more leads implanted by use of conventional transvenous delivery approaches. In another implementation, for example, one or more subcutaneous electrode subsystems or electrode arrays may be used to sense cardiac activity and deliver cardiac stimulation energy in an ITCS device configuration employing an active can or a configuration employing a non-active can. Electrodes may be situated at anterior and/or posterior locations relative to the heart.

An ITCS device may be used to implement various diagnostic functions. Subcutaneous, cutaneous, and/or external sensors, such as those previously described, may be employed to acquire physiologic and non-physiologic information for purposes of coordinated control of gas therapy, as well as enhancing tachyarrhythmia detection and termination.

In FIG. 10, there is shown a configuration of ITCS device having components implanted in the chest region of a patient at different locations. In the particular configuration shown in FIG. 10, the ITCS device includes the housing 1072 within which various cardiac sensing, detection, processing, and energy delivery circuitry may be housed. It is understood that the components and functionality depicted in the figures and described herein may be implemented in hardware, software, or a combination of hardware and software. It is further understood that the components and functionality depicted as separate or discrete blocks/elements in the figures in general may be implemented in combination with other components and functionality, and that the depiction of such components and functionality in individual or integral form is for purposes of clarity of explanation, and not of limitation.

Communications circuitry may be disposed within the housing 1072 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 1072 is typically configured to include one or more electrodes (e.g., can electrode and/or indifferent electrode). Although the housing 1072 is typically configured as an active can, it is appreciated that a non-active can configuration may be implemented, in which case at least two electrodes spaced apart from the housing 1072 are employed.

In the configuration shown in FIG. 10, a subcutaneous electrode 1074 may be positioned under the skin in the chest region and situated distal from the housing 1072. The subcutaneous and, if applicable, housing electrode(s) may be positioned about the heart at various locations and orientations, such as at various anterior and/or posterior locations relative to the heart. The subcutaneous electrode 1074 is coupled to circuitry within the housing 1072 via a lead assembly 1076. One or more conductors (e.g., coils or cables) are provided within the lead assembly 1076 and electrically couple the subcutaneous electrode 1074 with circuitry in the housing 1072. One or more sense, sense/pace or defibrillation electrodes may be situated on the elongated structure of the electrode support, the housing 1072, and/or the distal electrode assembly (shown as subcutaneous electrode 1074 in the configuration shown in FIG. 10).

In one configuration, the electrode support assembly and the housing 1072 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the electrode support assembly defines a physically separable unit relative to the housing 1072. The electrode support assembly includes mechanical and electrical couplings that facilitate mating engagement with corresponding mechanical and electrical couplings of the housing 1072. For example, a header block arrangement may be configured to include both electrical and mechanical couplings that provide for mechanical and electrical connections between the electrode support assembly and housing 1072. The header block arrangement may be provided on the housing 1072 or the electrode support assembly. Alternatively, a mechanical/electrical coupler may be used to establish mechanical and electrical connections between the electrode support assembly and housing 1072. In such a configuration, a variety of different electrode support assemblies of varying shapes, sizes, and electrode configurations may be made available for physically and electrically connecting to a standard ITCS device housing 1072.

Various embodiments disclosed herein may be used in connection with subcutaneous monitoring, diagnosis, and/or therapy. Methods, structures, and/or techniques described herein relating to subcutaneous systems and methods may incorporate features of one or more of the following references: commonly owned U.S. patent applications: "Subcutaneous Cardiac Sensing, Stimulation, Lead Delivery, and Electrode Fixation Systems and Methods," Ser. No. 60/462,272, filed Apr. 11, 2003; "Reconfigurable Subcutaneous Cardiac Device," Ser. No. 10/821,248, filed Apr. 8, 2004; and "Subcutaneous Cardiac Rhythm Management," Ser. No. 10/820,642, filed Apr. 8, 2004; each hereby incorporated herein by reference.

Figure 11:
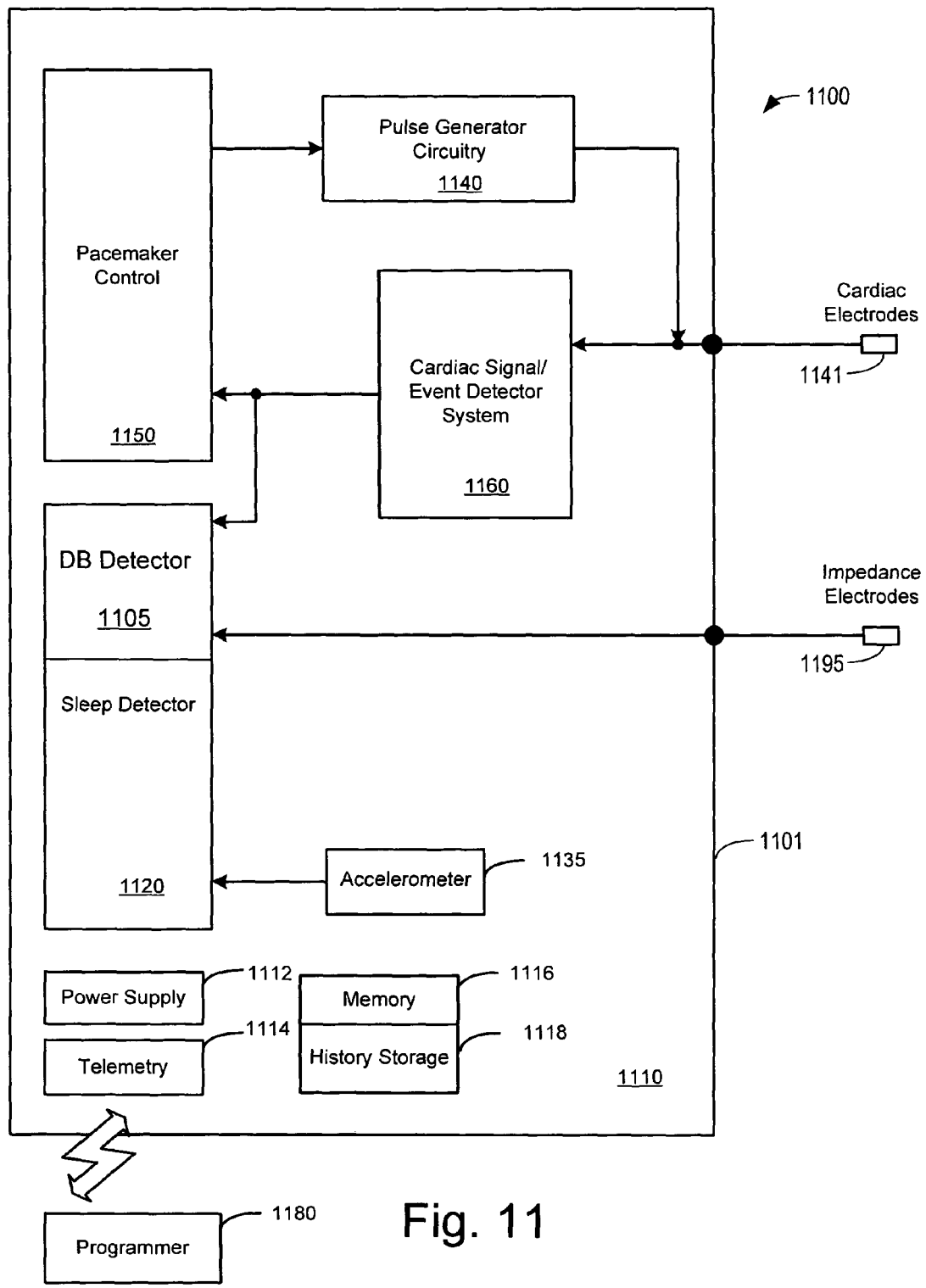
FIG. 11 is a block diagram of a cardiac rhythm management system configured as a pacemaker and suitable for implementing a sleep detection methodology in accordance with embodiments of the present invention.

Referring now to FIG. 11, there is shown a block diagram of an embodiment of a CRM system 1100 configured as a pacemaker and suitable for controlled gas therapy in accordance with the present invention. FIG. 11 shows the CRM 1100 divided into functional blocks. The CRM 1100 includes a sleep detector 1120 for receiving sleep-related signals and detecting sleep in accordance with embodiments of the present invention. The CRM 1100 also includes a disordered breathing detector 1105 that detects and/or predicts disordered breathing. The DB detector 1105 may also be configured to discern between types of disordered breathing (e.g., central versus obstructive apnea), and may also determine the severity of disordered breathing.

In one embodiment, the sleep detector 1120 is incorporated as part of CRM circuitry 1110 encased and hermetically sealed in a housing 1101 suitable for implanting in a human body. Power to the CRM 1100 is supplied by an electrochemical battery power supply 1112 housed within the CRM 1100. A connector block (not shown) is additionally attached to the CRM 1100 to allow for the physical and electrical attachment of the cardiac lead system conductors to the CRM circuitry 1110.

The CRM circuitry 1110 may be configured as a programmable microprocessor-based system, with circuitry for detecting sleep and disordered breathing in addition to providing pacing therapy to the heart. Cardiac signals sensed by one or more cardiac electrodes 1141 may be processed by the cardiac event detection circuitry 1160. Pace pulses controlled by the pacemaker control 1150 and generated by the pulse generator 1140 are delivered to the heart to treat various arrhythmias of the heart.

The memory circuit 1116 may store parameters for various device operations involved in sleep detection and/or cardiac pacing and sensing. The memory circuit 1116 may also store data indicative of sleep-related signals received by components of the CRM circuitry 1110, such as information derived from one or more impedance electrodes 1195, the cardiac signal detector system 1160, the accelerometer 1135, and/or the sleep detector 1120. The memory circuitry 1116 may also store data indicative of disordered breathing, such as information acquired and processed by the DB detector 1105.

As illustrated in FIG. 11, the sleep detector 1120 receives signals derived from the cardiac event detector 1160, the impedance electrodes 1195 and the accelerometer 1135 to perform operations involving detecting sleep onset and sleep termination according to the principles of the present invention. Historical data storage 1118 may be coupled to the sleep detection circuitry 1120 for storing historical sleep related data. Historical data storage 1118 may also be coupled to the DB detector 1105 for storing historical disordered breathing related data. Such data may be transmitted to an external programmer unit 1180 (or external server system) and used for various diagnostic purposes and as needed or desired.

Telemetry circuitry 1114 is coupled to the CRM circuitry 1110 to allow the CRM 1100 to communicate with a remote device such as the programmer 1180, or other device. In one embodiment, the telemetry circuitry 1114 and the programmer 1180 use a wire loop antenna and a radio frequency telemetric link to receive and transmit signals and data between the programmer 1180 and telemetry circuitry 1114. In this manner, programming commands and data may be transferred between the CRM circuitry 1110 and the one or more remote devices 1180 during and after implant.

The programming commands allow a physician to set or modify various parameters used by the CRM system 1100. These parameters may include setting sleep detection parameters for use during sleep detection, such as which sleep-related signals are to be used for sleep detection and threshold adjustment, and the initial sleep detection thresholds. In addition, the CRM system 1100 may download to the programmer 1180 stored data pertaining to sensed sleep periods, including the amount of time spent sleeping, the time of day sleep periods occurred, historical data of sleep times, and the number of arousals during the sleep periods, for example. Other parameters may include disordered breathing detection and therapy parameters. For example, parameters associated with disordered breathing may be downloaded to the programmer 1180. Disordered breathing data may be stored regarding the severity, frequency, and occurrences of disordered breathing, for example. Signals representing detected disordered breathing events may be stored.

Still referring to FIG. 11, signals associated with patient activity may be detected through the use of an accelerometer 1135 positioned within the housing 1101 of the CRM 1100. The accelerometer 1135 may be responsive to patient activity. The accelerometer signal may be correlated with activity level or workload, for example. Signals derived from the accelerometer 1135 are coupled to the sleep detector 1120 and may also be used by the pacemaker 1150 for implementing a rate adaptive pacing regimen, for example.

The impedance electrodes 1195 sense the patient's transthoracic impedance. The transthoracic impedance may be used to calculate various parameters associated with respiration. Impedance driver circuitry (not shown) induces a current that flows through the blood between the impedance drive electrode and a can electrode on the housing 1101 of the CRM 1100. The voltage at an impedance sense electrode relative to the can electrode changes as the transthoracic impedance changes. The voltage signal developed between the impedance sense electrode and the can electrode is detected by the impedance sense amplifier and is delivered to the sleep detector circuitry 1120 for further processing. The impedance electrodes 1195 may also be used in conjunction with the DB detector 1105. As discussed previously, arousal and other episodes of breathing disorders (e.g., hypopnea, apnea) may be determined using an impedance signal developed by the impedance electrodes 1195.

FIG. 12 is a block diagram of a medical system 1200 that may be used to implement coordinated patient measuring and/or monitoring, diagnosis, and/or therapy, including detection of blood gas levels and coordinated control of gas therapy systems in accordance with embodiments of the present invention. The medical system 1200 may include, for example, one or more patient-internal medical devices 1210 and one or more patient-external medical devices 1220. Each of the patient-internal 1210 and patient-external 1220 medical devices may include one or more of a patient monitoring unit 1212, 1222, a diagnostics unit 1214, 1224, and/or a therapy unit 1216, 1226.

The patient-internal medical device 1210 is typically a fully or partially implantable device that performs measuring, monitoring, diagnosis, and/or therapy functions. The patient-external medical device 1220 performs monitoring, diagnosis and/or therapy functions external to the patient (i.e., not invasively implanted within the patient's body). The patient-external medical device 1220 may be positioned on the patient, near the patient, or in any location external to the patient. It is understood that a portion of a patient-external medical device 1220 may be positioned within an orifice of the body, such as the nasal cavity or mouth, yet may be considered external to the patient (e.g., mouth pieces/appliances, tubes/appliances for nostrils, or temperature sensors positioned in the ear canal).

The patient-internal and patient-external medical devices 1210, 1220 may be coupled to one or more sensors 1241, 1242, 1245, 1246, patient input devices 1243, 1247 and/or other information acquisition devices 1244, 1248. The sensors 1241, 1242, 1245, 1246, patient input devices 1243, 1247, and/or other information acquisition devices 1244, 1248 may be employed to detect diseases/disorders relevant to the monitoring, diagnostic, and/or therapeutic functions of the patient-internal and patient-external medical devices 1210, 1220.

The medical devices 1210, 1220 may each be coupled to one or more patient-internal sensors 1241, 1245 that are fully or partially implantable within the patient. The medical devices 1210, 1220 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 1241 may be coupled to the patient-internal medical device 1210 through one or more internal leads 1253. In one example, as was described above with reference to FIG. 9, an internal endocardial lead system is used to couple cardiac electrodes to an implantable pacemaker or other cardiac rhythm management device. Still referring to FIG. 12, one or more patient-internal sensors 1241 may be equipped with transceiver circuitry to support wireless communications between the one or more patient-internal sensors 1241 and the patient-internal medical device 1210 and/or the patient-external medical device 1220. The patient-external sensors 1242 may be coupled to the patient-internal medical device 1210 and/or the patient-external medical device 1220 through one or more internal leads 1255 or through wireless connections. Patient-external sensors 1242 may communicate with the patient-internal medical device 1210 wirelessly. Patient-external sensors 1246 may be coupled to the patient-external medical device 1220 through one or more internal leads 1257 or through a wireless link.

The medical devices 1210, 1220 may be coupled to one or more patient input devices 1243, 1247. The patient input devices are used to allow the patient to manually transfer information to the medical devices 1210, 1220. The patient input devices 1243, 1247 may be particularly useful for inputting information concerning patient perceptions, such as how well the patient feels, and information such as patient smoking, drug use, or other activities that are not automatically sensed or detected by the medical devices 1210, 1220.

The medical devices 1210, 1220 may be connected to one or more information acquisition devices 1244, 1248, for example, a database that stores information useful in connection with the monitoring, diagnostic, or therapy functions of the medical devices 1210, 1220. For example, one or more of the medical devices 1210, 1220 may be coupled through a network to a patient information server 1230 that provides information about environmental conditions affecting the patient, e.g., the pollution index for the patient's location.

In one embodiment, the patient-internal medical device 1210 and the patient-external medical device 1220 may communicate through a wireless link between the medical devices 1210, 1220. For example, the patient-internal and patient-external devices 1210, 1220 may be coupled through a short-range radio link, such as Bluetooth, IEEE 802.11, and/or a proprietary wireless protocol. The communications link may facilitate unidirectional or bidirectional communication between the patient-internal 1210 and patient-external 1220 medical devices. Data and/or control signals may be transmitted between the patient-internal 1210 and patient-external 1220 medical devices to coordinate the functions of the medical devices 1210, 1220.

In another embodiment, the patient-internal and patient-external medical devices 1210, 1220 may be used within the structure of an advanced patient management system 1240. Advanced patient management systems 1240 involve a system of medical devices that are accessible through various communications technologies. For example, patient data may be downloaded from one or more of the medical devices periodically or on command, and stored at the patient information server 1230. The physician and/or the patient may communicate with the medical devices and the patient information server 1230, for example, to acquire patient data or to initiate, terminate or modify therapy.

The data stored on the patient information server 1230 may be accessible by the patient and the patient's physician through one or more terminals 1250, e.g., remote computers located in the patient's home or the physician's office. The patient information server 1230 may be used to communicate to one or more of the patient-internal and patient-external medical devices 1210, 1220 to provide remote control of the monitoring, diagnosis, and/or therapy functions of the medical devices 1210, 1220.

In one embodiment, the patient's physician may access patient data transmitted from the medical devices 1210, 1220 to the patient information server 1230. After evaluation of the patient data, the patient's physician may communicate with one or more of the patient-internal or patient-external devices 1210, 1220 through the APM system 1240 to initiate, terminate, or modify the monitoring, diagnostic, and/or therapy functions of the patient-internal and/or patient-external medical systems 1210, 1220. Systems and methods involving advanced patient management techniques are further described in U.S. Pat. Nos. 6,336,903, 6,312,378, 6,270,457, and 6,398,728, hereby incorporated herein by reference.

In another embodiment, the patient-internal and patient-external medical devices 1210, 1220 may not communicate directly, but may communicate indirectly through the APM system 1240. In this embodiment, the APM system 1240 may operate as an intermediary between two or more of the medical devices 1210, 1220. For example, data and/or control information may be transferred from one of the medical devices 1210, 1220 to the APM system 1240. The APM system 1240 may transfer the data and/or control information to another of the medical devices 1210, 1220.

In one embodiment, the APM system 1240 may communicate directly with the patient-internal and/or patient-external medical devices 1210, 1220. In another embodiment, the APM system 1240 may communicate with the patient-internal and/or patient-external medical devices 1210, 1220 through medical device programmers 1260, 1270 respectively associated with each medical device 1210, 1220.

Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks may be arranged and implemented. The examples depicted herein provide examples of possible functional arrangements used to implement the approaches of the invention.

Each feature disclosed in this specification (including any accompanying claims, abstract, and drawings), may be replaced by alternative features having the same, equivalent or similar purpose, unless expressly stated otherwise. Thus, unless expressly stated otherwise, each feature described is one example only of a generic series of equivalent or similar features.

While preferred embodiments of the present invention have been shown and described herein, it will be obvious to those skilled in the art that such embodiments are provided by way of example only. Numerous variations, changes, and substitutions will be apparent to those skilled in the art without departing from the invention. Accordingly, it is intended that the invention be limited only by the spirit and scope of the appended claims.

What is claimed is:

1. A therapy method, comprising:
controlling delivery of a gas therapy delivered by a gas therapy delivery unit to a patient's pulmonary system, the gas therapy involving delivery of a first gas;
sensing concentration of a blood gas;
detecting a disorder based on the blood gas concentration; and
adapting the gas therapy by modifying delivery of a second gas, different from the first gas, to treat the detected disorder,
wherein at least one of sensing the blood gas concentration and adapting the gas therapy is performed at least in part implantably by a cardiac rhythm management device having a therapy controller, and wherein the therapy controller is wirelessly coupled to the gas therapy delivery unit.

2. The method of claim 1, wherein both of sensing the blood gas concentration and adapting the gas therapy are performed at least in part implantably.

3. The method of claim 1, wherein the disorder comprises disordered breathing.

4. The method of claim 1, wherein:
the disorder comprises disordered breathing; and
the second gas comprises carbon dioxide.

5. The method of claim 4, further comprising:
discerning a type of the detected disordered breathing;
wherein adapting the gas therapy comprises adapting the gas therapy responsive to the disordered breathing type.

6. The method of claim 5, further comprising
discerning the type of disordered breathing comprises discerning central apnea from obstructive apnea.

7. The method of claim 6, wherein adapting the gas therapy comprises applying the carbon dioxide to the patient's system through a positive airway pressure device if the disordered breathing type is central apnea.

8. The method of claim 1, wherein adapting the gas therapy comprises increasing or decreasing a pressure of the first gas during adapted gas therapy delivery.

9. The method of claim 1, wherein adapting the gas therapy comprises one or more of introducing, terminating, or adjusting concentration of the first fed through a positive airway pressure device.

10. The method of claim 1, wherein:
detecting the disorder comprises detecting hypoxemia; and
adapting the gas therapy comprises initiating introduction of oxygen to the patient's pulmonary system to treat the hypoxemia.

11. The method of claim 1, wherein:
the detected disorder comprises hypocapnia and the adapted gas therapy is delivered to treat the hypocapnia.

12. The method of claim 1, wherein:
the detected disorder comprises ischemia and
the adapted gas therapy is delivered to treat the ischemia.

13. The method of claim 12, wherein the implantable cardiac rhythm management device delivers a cardiac electrical therapy to treat the ischemia.

14. The method of claim 1, wherein the second gas comprises a vasodilator or a bronchodilator.

15. A gas therapy system, comprising:
a sensor configured to sense concentration of a blood gas;
a detector configured to detect a disorder based on the concentration of blood gas;
a therapy controller coupled to the sensor and configured to control delivery of a gas therapy involving a first gas, and to adapt the gas therapy by modifying delivery of a second gas, different from the first gas to treat the detected disorder;
a gas therapy delivery unit coupled to the therapy controller and configured to deliver the adapted gas therapy to the patient's pulmonary system; and
an implantable cardiac rhythm management device;
wherein at least one of the sensor and the controller comprises an implantable component coupled to the implantable cardiac rhythm management device, and wherein the therapy controller is wirelessly coupled to the gas therapy delivery unit.

16. The gas therapy system of claim 15, wherein each of the sensor and the therapy controller comprises an implantable component.

17. The gas therapy system of claim 15, wherein the implantable cardiac rhythm management device is an implantable cardiac therapy device, and the sensor is a component of the implantable cardiac therapy device.

18. The gas therapy system of claim 15, wherein the sensor is a component of a patient-external respiratory therapy device.

19. The gas therapy system of claim 15, wherein the sensor is a component of a positive airway pressure device.

20. The gas therapy system of claim 15, wherein the sensor comprises one or both of a blood oxygen sensor or a carbon dioxide sensor.

21. The gas therapy system of claim 15, wherein the implantable cardiac rhythm management device is an implantable cardiac therapy device, and the sensor comprises one or both of an implantable blood oxygen sensor or an implantable carbon dioxide sensor coupled to the implantable cardiac therapy device.

22. The gas therapy system of claim 15, wherein the sensor is wirelessly coupled to the therapy controller.

23. The gas therapy system of claim 15, wherein the sensor is coupled to the controller through the gas therapy delivery unit.

24. The gas therapy system of claim 15, wherein the gas therapy delivery unit comprises one or both of a vasodilating agent delivery arrangement or a bronchodilator agent delivery arrangement.

25. A therapy system, comprising:
means for sensing concentration of a blood gas;

means for determining a disorder of the patient based on the concentration of the blood gas;
means for controlling delivery of a gas therapy comprising a first gas and for adapting the gas therapy, responsive to the detected disorder, by controlling delivery of a second gas, different from the first gas;
means for delivering the adapted gas therapy to a patient by delivering a gas to the patient's pulmonary system,
wherein at least one of the sensing means and the adapting means comprises an implantable component, and wherein the means for controlling the gas therapy is wirelessly coupled to the means for delivering the adapted gas therapy.

26. The therapy system of claim 25, wherein the detected disorder is disordered breathing and the second gas comprises carbon dioxide.

27. The therapy system of claim 25, wherein the second gas comprises a vasodialation or bronchiodialation agent.

* * * * *

UNITED STATES PATENT AND TRADEMARK OFFICE
CERTIFICATE OF CORRECTION

| | | |
|---|---|---|
| PATENT NO. | : 8,251,061 B2 | Page 1 of 1 |
| APPLICATION NO. | : 10/929306 | |
| DATED | : August 28, 2012 | |
| INVENTOR(S) | : Kent Lee et al. | |

It is certified that error appears in the above-identified patent and that said Letters Patent is hereby corrected as shown below:

Column 19, line 66, Claim 9: "first fed" should read --first gas fed--.

Signed and Sealed this
Twenty-seventh Day of November, 2012

David J. Kappos
*Director of the United States Patent and Trademark Office*